United States Patent
Black et al.

(10) Patent No.: US 6,222,048 B1
(45) Date of Patent: Apr. 24, 2001

(54) DIARYL-2-(5H)-FURANONES AS COX-2 INHIBITORS

(75) Inventors: Cameron Black; Erich Grimm; Serge Leger; Petpiboon Prasit; Zhaoyin Wang, all of Kirkland (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/011,674

(22) PCT Filed: Dec. 18, 1995

(86) PCT No.: PCT/CA95/00715

§ 371 Date: Jun. 12, 1997

§ 102(e) Date: Jun. 12, 1997

(87) PCT Pub. No.: WO96/19469

PCT Pub. Date: Jun. 27, 1996

(51) Int. Cl.[7] ............... C07D 307/58; C07D 307/94; C07D 407/04; A61K 31/34; A61K 31/365; A61K 31/381

(52) U.S. Cl. ................ 549/60; 514/326; 514/438; 514/461; 546/16; 546/214; 546/284.4; 548/169; 548/207; 548/517; 549/60; 549/268; 549/295; 549/320; 549/462

(58) Field of Search ........................ 549/295, 320, 549/60, 462, 268; 514/326, 461, 438; 548/169, 207, 517; 546/16, 214, 284.4

(56) References Cited

U.S. PATENT DOCUMENTS 5,474,995 * 12/1995 Ducharme et al. ............... 514/241

* cited by examiner

*Primary Examiner*—Floyd D. Higel
(74) *Attorney, Agent, or Firm*—Raynard Yuro; David L. Rose

(57) ABSTRACT

The invention encompasses the novel compound of Formula (I) as well as a method of treating cyclooxygenase-2 mediated diseases comprising administration to a patient in need of such treatment of a non-toxic therapeutically effective amount of a compound of Formula (I). The invention also encompasses certain pharmaceutical compositions for treatment of cyclooxygenase-2 mediated diseases comprising compounds of Formula (I).

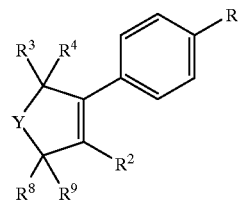

20 Claims, No Drawings

DIARYL-2-(5H)-FURANONES AS COX-2 INHIBITORS

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 or the constitutive enzyme, as originally identified in bovine seminal vesicles. More recently the gene for a second inducible form of cyclooxygenase (cyclooxygenase-2) has been cloned, sequenced and characterized initially from chicken, murine and human sources. This enzyme is distinct from the cyclooxygenase-1 which has been cloned, sequenced and characterized from various sources including the sheep, the mouse and man. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

A brief description of the potential utilities of cyclooxygenase-2 inhibitors is given in an article by John Vane, *Nature*, Vol. 367, pp. 215–216, 1994 and in an article in *Drug News and Perspectives*, Vol. 7, pp. 501–512, 1994.

SUMMARY OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

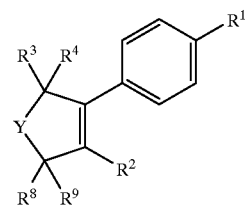

The invention also encompasses certain pharmaceutical compositions for treatment of cyclooxygenase-2 mediated diseases comprising compounds of Formula I.

DETAILED DESCRIPTION OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

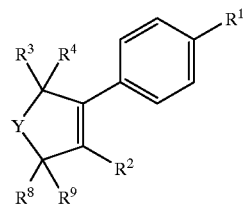

I or a pharmaceutically acceptable salt thereof wherein:
Y is selected from the group consisting of
 (a) $C(R^{10})(R^{11})$,
 (b) oxygen,
 (c) sulfur,
$R^1$ is selected from the group consisting of
 (a) $S(O)_2CH_3$,
 (b) $S(O)_2NH_2$,
 (c) $S(O)_2NHC(O)CF_3$,
 (d) $S(O)(NH)NH_2$,
 (e) $S(O)(NH)NHC(O)CF_3$,
 (f) $P(O)(CH_3)NH_2$,
 (g) $P(O)(CH_3)_2$,
$R^2$ is selected from the group consisting of
 (a) $C_{1-6}$alkyl,
 (b) $C_{3-7}$ cycloalkyl,
 (c) mono-, di- or tri-substituted phenyl or naphthyl wherein the substituent is selected from the group consisting of
  (1) hydrogen,
  (2) halo,
  (3) $C_{1-6}$alkoxy,
  (4) $C_{1-6}$alkylthio,
  (5) CN,
  (6) $CF_3$,
  (7) $C_{1-6}$alkyl,
  (8) $N_3$,
  (9) —$CO_2H$,
  (10) —$CO_2$—$C_{1-4}$alkyl,
  (11) —$C(R^5)(R^6)$—OH,
  (12) —$C(R^5)(R^6)$—O—$C_{1-4}$alkyl, and
  (13) —$C_{1-6}$alkyl—$CO_2$—$R^5$;

(14) benzyloxy,
(15) —O—($C_{1-6}$alkyl)—$CO_2R^5$,
(16) —O—($C_{1-6}$alkyl)-$NR^5R^6$, (d) mono-, di- or tri-substituted heteroaryl wherein the heteroaryl is a monocyclic aromatic ring of 5 atoms, said ring having one hetero atom which is S, O, or N, and optionally 1, 2, or 3 additionally N atoms; or
the heteroaryl is a monocyclic ring of 6 atoms, said ring having one hetero atom which is N, and optionally 1, 2, 3, or 4 additional N atoms, said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH, and
(10) —$C(R^5)(R^6)$—O—$C_{1-4}$alkyl;

(e) a mono- or di-substituted benzoheterocycle in which the heterocycle is a 5, 6, or 7-membered ring which may contain 1 or 2 heteroatoms chosen independently from O, S, or N and which may contain a carbonyl group or a sulfonyl group; the said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH, and
(10) —$C(R^5)(R^6)$—O—$C_{1-4}$alkyl;

(f) a heterocycloalkyl group of 5, 6 or 7 members which contains 1 or 2 heteroatoms chosen from O, S, or N and optionally contains a carbonyl group or a sulfonyl group.

(g) a mono- or di-substituted benzocarbocycle in which the carbocycle is a 5, 6, or 7-membered ring which optionally contains a carbonyl group, the said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH, and
(10) —$C(R^5)(R^6)$—O—$C_{1-4}$alkyl;

$R^3$ is $C_{1-7}$alkyl, $CH_2OR^7$, CN, $CH_2CN$, or $C_{1-6}$fluoroalkyl, F, $CONR^7_2$, mono- or di-substituted phenyl, mono or di-substituted benzyl, mono- or di-substituted heteroaryl, mono or di-substituted heteroarylmethyl, wherein the substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH, and
(10) —$C(R^5)R^6)$—O—$C_{1-4}$alkyl;

$R^4$ is
(a) mono- or di-substituted phenyl or mono- or di-substituted benzyl or mono or di-substituted heteroaryl or mono-or di-substituted heteroarylmethyl, said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH, and
(10) —$C(R^5)(R^6)$—O—$C_{1-4}$alkyl, or (b) $C_{1-7}$alkyl, $CH_2OR^7$, CN, $CH_2CN$, or $C_{1-6}$fluoroalkyl, F or $CONR^7_2$; or $R^3$ and $R^4$ together with the carbon to which they are attached form a saturated monocyclic ring of 3, 4, 5, 6 or 7 atoms, optionally containing 1 or 2 heteroatoms chosen independently from O, S, N, and optionally hexa-substituted by $R^{12}$ and optionally containing a carbonyl or sulfonyl group, each $R^{12}$ is independently selected from the group consisting of
(a) hydrogen,
(b) $C_{1-6}$alkyl,
(c) phenyl or monosubstituted phenyl wherein the substituents may be halo, $C_{1-6}$alkyl, $C_{1-6}$alkoxy, $C_{1-6}$alkylthio, CN, or $CF_3$,
(d) benzyl or monosubstituted benzyl wherein the substituents may be halo, $C_{1-6}$alkyl, $C_{1-6}$alkoxy, $C_{1-6}$alkylthio, CN, or $CF_3$,
(e) —$CO_2$-alkyl,
(f) halo;

$R^5$, $R^6$ and $R^7$ are each independently selected from the group consisting of
(a) hydrogen, and
(b) $C_{1-6}$alkyl,
or $R^5$ and $R^6$ together with the carbon to which they are attached form a saturated monocyclic carbon ring of 3, 4, 5, 6 or 7 atoms;

$R^8$ and $R^9$ are independently selected from the group consisting of:
(a) hydrogen,
(b) $C_{1-7}$alkyl, or
$R^8$ and $R^9$ together form a double bonded O or S;

$R^{10}$ and $R^{11}$ are independently
(a) hydrogen,
(b) mono- or di-substituted phenyl or mono- or di-substituted benzyl or mono- or di-substituted heteroaryl or mono- or di-substituted heteroarylmethyl, said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio, (6) CN,
(7) CF$_3$,
(8) N$_3$,
(9) —C(R$^{13}$)(R$^{14}$)—OH, and
(10) —C(R$^{13}$)(R$^{14}$)—O—C$_{1-4}$alkyl, or (c) C$_{1-7}$alkyl, CH$_2$OR$^7$, CN, CH$_2$CN, C$_{1-6}$fluoroalkyl, F or CONR$^7_2$; or R$^{10}$ and R$^{11}$ together with the carbon to which they are attached form a carbonyl or a saturated monocyclic carbon ring of 3, 4, 5, 6 or 7 atoms;

R$^{13}$ and R$^{14}$ are independently selected from the group consisting of:

(a) hydrogen,
(b) C$_{1-7}$alkyl, or

R$^{13}$ and R$^{14}$ together with the carbon to which they are attached to form a carbonyl, —C(=S)—, or a saturated monocyclic carbon ring of 3, 4, 5, 6, or 7 atoms, with the proviso that when Y is O or S, and R$^8$ and R$^9$ are taken together with the carbon to which they are attached to form a carbonyl, and R$^3$ and R$^4$ are each methyl, then R$^2$ is other than a 2-naphthyl or an optionally mono or di-substituted phenyl, wherein the substituent is meta-fluoro, para-fluoro, meta-chloro or para-chloro; or 3,4-dichloro or 3,4-difluoro; and with the further proviso that when R$^3$ and R$^4$ taken together with the carbon to which they are attached form a carbonyl, then R$^8$ and R$^9$ taken together with the carbon to which they are attached form a group other than carbonyl.

For purposes of this specification heteroaryl as in R$^2$ is intended to include, but is not limited to optionally mono- or di-substituted (1) furanyl,
(2) diazinyl, triazinyl, tetrazinyl,
(3) imidazolyl,
(4) isooxazolyl,
(5) isothiazolyl,
(6) oxadiazolyl,
(7) oxazolyl,
(8) pyrazolyl,
(9) pyrrolyl,
(10) thiadiazolyl,
(11) thiazolyl,
(12) thienyl,
(13) triazolyl, or
(14) tetrazolyl.

Similarly, for purposes of this specification cyclic groups such as a heterocycloalkyl or benzocarbocycle or benzoheterocycle such as in R$^2$ is intended to include, but is not limited to optionally mono- or di-substituted (1) 2-indolyl,
(2) 3-indolyl,
(3) 1-methyl-5-indolyl
(4) 2-benzofuranyl,
(5) 3-benzofuranyl,
(6) 5-benzofuranyl,
(7) 6-benzofuranyl,
(8) 2-benzothienyl,
(9) 3-benzothienyl,
(10) 5-benzothienyl,
(11) 6-benzothienyl,

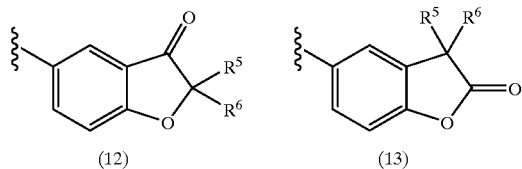

(12)

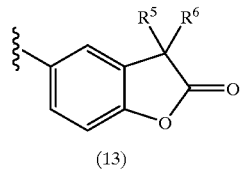

(13)

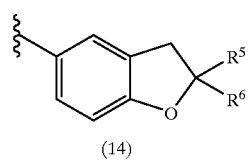

(14)

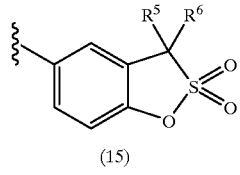

(15)

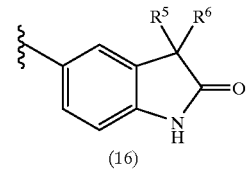

(16)

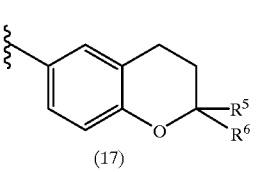

(17)

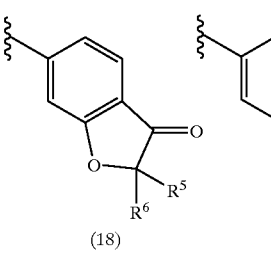

(18)

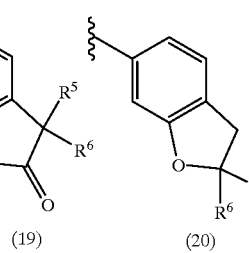

(19)

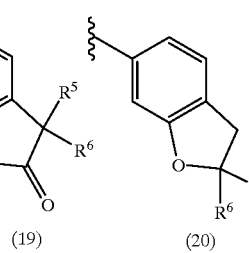

(20)

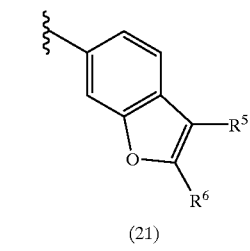

(21)

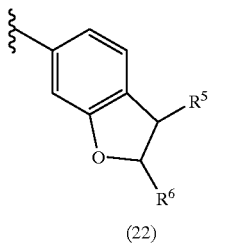

(22)

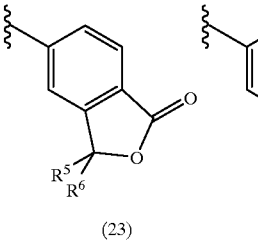

(23)

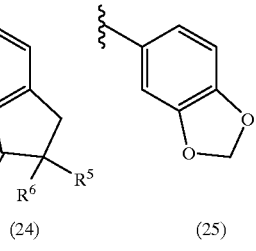

(24)

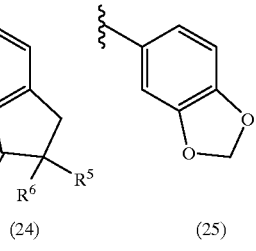

(25)

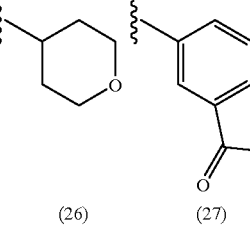

(26)

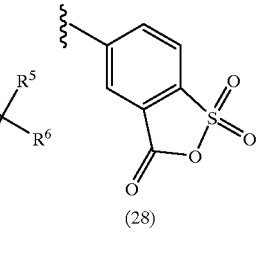

(27)

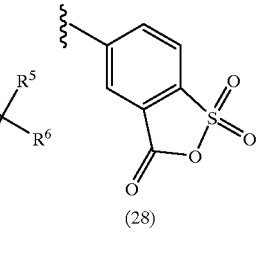

(28)

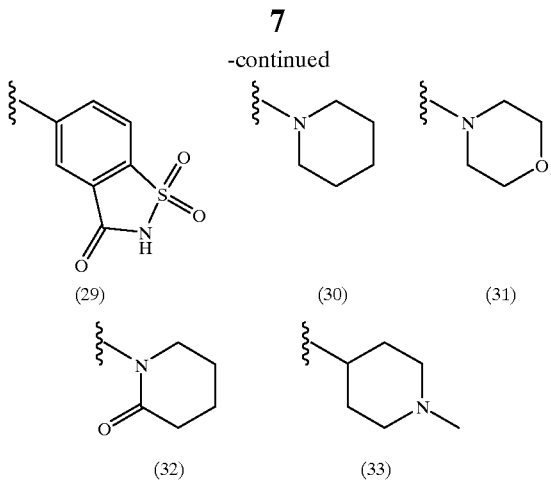

(29) (30) (31)

(32) (33)

One genus of compounds of formula I is that in which $R^8$ and $R^9$ form a double-bonded O, Y is O.

Another genus is that in which $R^2$ is a mono-, di- or tri-substituted phenyl or naphthyl, and the remaining substituents are as defined for structure I.

Within this genus there is a class of compounds wherein wherein:

Y is O, $R^1$ is selected from the group consisting of
(a) $S(O)_2CH_3$,
(b) $S(O)_2NH_2$,
(c) $S(O)_2NHC(O)CF_3$,
(d) $S(O)(NH)NH_2$,
(e) $S(O)(NH)NHC(O)CF_3$,
(f) $P(O)(CH_3)NH_2$,
(g) $P(O)(CH3)2$ $R^2$ is selected from the group consisting of
mono-, di- or tri-substituted phenyl or naphthyl wherein the substituent is selected from the group consisting of
(1) hydrogen,
(2) halo,
(3) $C_{1-4}$alkoxy,
(4) $C_{1-4}$alkylthio,
(5) CN,
(6) $CF_3$,
(7) $C_{1-4}$alkyl,
(8) $N_3$,
(9) —$CO_2H$,
(10) —$CO_2$—$C_{1-4}$alkyl,
(11) —$C(R^5)(R^6)$—OH,
(12) —$C(R^5)(R^6)$—O—$C_{1-4}$alkyl, and
(13) —$C_{1-6}$alkyl-$CO_2$—$R^5$,
(14) benzyloxy,
(15) —O—($C_{1-4}$alkyl)-$CO_2R^5$,
(16) —O—($C_{1-4}$alkyl)—$NR^5R^6$;

$R^3$ is $CH_2OR^7$, CN, $CH_2CN$, or $C_{1-6}$fluoroalkyl;

$R^4$ is
(a) substituted phenyl or substituted heteroaryl, said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$, (9) —$C(R^5)(R^6)$—OH, and
(10) —$C(R^5)(R^6)$—O—$C_{1-4}$alkyl, or
(b) $C_{1-6}$alkyl, $CH_2OR^7$, CN, $CH_2CN$, or $C_{1-6}$fluoroalkyl; or $R^3$ and $R^4$ together with the carbon to which they are attached form a saturated monocyclic ring of 3, 4, 5, 6 or 7 atoms, optionally containing 1 or 2 heteroatoms chosen independently from O, S, N, and optionally substituted by tetra-$R^{12}$, each $R^{12}$ is independently selected from the group consisting of
(a) hydrogen,
(b) $C_{1-6}$alkyl,
(c) phenyl or monosubstituted phenyl wherein the substituents may be halo, $C_{1-6}$alkyl, $C_{1-6}$alkoxy, $C_{1-6}$alkylthio, CN, or $CF_3$,
(d) benzyl or monosubstituted benzyl wherein the substituents may be halo, $C_{1-6}$alkyl, $C_{1-6}$alkoxy, $C_{1-6}$alkylthio, CN, or $CF_3$,
(e) —$CO_2$-alkyl,
(f) halo, $R^5$, $R^6$ and $R^7$ are each independently selected from the group consisting of
(a) hydrogen, and
(b) $C_{1-6}$alkyl,
or $R^5$ and $R^6$ together with the carbon to which they are attached form a saturated monocyclic carbon ring of 3, 4, 5, 6 or 7 atoms.

Within this class are the compounds wherein $R^1$ is selected from the group consisting of
(a) $S(O)_2CH_3$,
(b) $S(O)_2NH_2$, $R^2$ is selected from the group consisting of
mono-, di- or tri-substituted phenyl or naphthyl wherein the substituent is selected from the group consisting of
(1) hydrogen,
(2) halo,
(3) $C_{1-4}$alkoxy,
(4) $C_{1-4}$alkylthio,
(5) CN,
(6) $CF_3$,
(7) $C_{1-4}$alkyl,
(8) $N_3$, and
(9) —$C(R^5)R^6$)—OH;

$R^3$ is $CH_2OR^7$, CN, $CH_2CN$, or $C_{1-3}$fluoroalkyl;

$R^4$ is
(a) substituted phenyl or substituted heteroaryl, said substituents are selected from the group consisting of
(1) hydrogen,
(2) halo, including fluoro, chloro, bromo and iodo,
(3) $C_{1-3}$alkyl,
(4) $C_{1-3}$alkoxy,
(5) $C_{1-4}$alkylthio,
(6) CN,
(7) $CF_3$, or
(b) $C_{1-3}$alkyl, $CH_2OR^7$, CN, $CH_2CN$, or $C_{1-3}$fluoroalkyl;

$R^5$, $R^6$ and $R^7$ are each independently selected from the group consisting of
(a) hydrogen, and
(b) $C_{1-3}$alkyl.

Another genus of the invention encompasses compounds of formula Ib

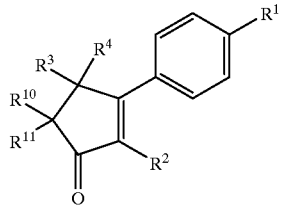

Ib wherein
Y is $C(R^{10})(R^{11})$;
$R^1$ is selected from the group consisting of
  (a) $S(O)_2CH_3$,
  (b) $S(O)_2NH_2$,
  (c) $S(O)_2NHC(O)CF_3$,
  (d) $S(O)(NH)NH_2$,
  (e) $S(O)(NH)NHC(O)CF_3$,
  (f) $P(O)(CH_3)NH_2$,
  (g) $P(O)(CH3)2$
$R^2$ is selected from the group consisting of
  cyclohexyl, and
  mono-, di- or tri-substituted phenyl or naphthyl wherein the substituent is selected from the group consisting of
    (1) hydrogen,
    (2) halo,
    (3) $C_{1-6}$alkoxy,
    (4) $C_{1-6}$alkylthio,
    (5) CN,
    (6) $CF_3$,
    (7) $C_{1-6}$alkyl,
    (8) $N_3$,
    (9) —$CO_2H$,
    (10) —$CO_2$—$C_{1-4}$alkyl,
    (11) —$C(R^5)(R^6)$—OH,
    (12) —$C(R^5)(R^6)$—O—$C_{1-4}$alkyl, and
    (13) —$C_{1-6}$alkyl-$CO_2$—$R^5$;
    (14) benzyloxy,
    (15) —O—($C_{1-6}$alkyl)-$CO_2R^5$
    (16) —O—($C_{1-6}$alkyl)—$NR^5R^6$
$R^3$ is $CH_2OR^7$, CN, $CH_2CN$, or $C_{1-6}$fluoroalkyl;
$R^4$ is
  (a) substituted phenyl or substituted heteroaryl, said substituents are selected from the group consisting of
    (1) hydrogen,
    (2) halo, including fluoro, chloro, bromo and iodo,
    (3) $C_{1-6}$alkyl,
    (4) $C_{1-6}$alkoxy,
    (5) $C_{1-6}$alkylthio,
    (6) CN,
    (7) $CF_3$,
    (8) $N_3$,
    (9) —$C(R^5)(R^6)$—OH, and
    (10) —$C(R^5)(R^6)$—O—$C_{1-4}$alkyl, or
  (b) $C_{1-6}$alkyl, $CH_2OR^7$, CN, $CH_2CN$, or $C_{1-6}$fluoroalkyl; or
$R^3$ and $R^4$ together with the carbon to which they are attached form a saturated monocyclic ring of 3, 4, 5, 6 or 7 atoms, optionally containing 1 or 2 heteroatoms chosen independently from O, S, N, and optionally substituted by tetra-$R^{12}$,
each $R^{12}$ is independently selected from the group consisting of
  (a) hydrogen,
  (b) $C_{1-6}$alkyl,
  (c) phenyl or monosubstituted phenyl wherein the substituents may be halo, $C_{1-6}$alkyl, $C_{1-6}$alkoxy, $C_{1-6}$alkylthio, CN, or $CF_3$,
  (d) benzyl or monosubstituted benzyl wherein the substituents may be halo, $C_{1-6}$alkyl, $C_{1-6}$alkoxy, $C_{1-6}$alkylthio, CN, or $CF_3$,
  (e) —$C_2$-alkyl,
  (f) halo,
$R^5$, $R^6$ and $R^7$ are each independently selected from the group consisting of
  (a) hydrogen, and
  (b) $C_{1-6}$alkyl,
  or $R^5$ and $R^6$ together with the carbon to which they are attached form a saturated monocyclic carbon ring of 3, 4, 5, 6 or 7 atoms;
$R^{10}$ and $R^{11}$ are independently
  (a) hydrogen,
  (b) substituted phenyl or substituted heteroaryl, said substituents are selected from the group consisting of
    (1) hydrogen,
    (2) halo, including fluoro, chloro, bromo and iodo,
    (3) $C_{1-6}$alkyl,
    (4) $C_{1-6}$alkoxy,
    (5) $C_{1-6}$alkylthio,
    (6) CN,
    (7) $CF_3$,
    (8) $N_3$,
    (9) —$C(R^{13})(R^{14})$—OH, and
    (10) —$C(R^{13})(R^{14})$—O—$C_{1-4}$alkyl, or
  (c) $C_{1-7}$alkyl, $CH_2OR^7$, CN, $CH_2CN$, or $C_{1-6}$fluoroalkyl; or
$R^{10}$ and $R^{11}$ together with the carbon to which they are attached form a saturated monocyclic carbon ring of 3, 4, 5, 6 or 7 atoms;
$R^{13}$ and $R^{14}$ are independently selected from the group consisting of:
  (a) hydrogen,
  (b) $C_{1-6}$alkyl, or
  $R^{13}$ and $R^{14}$ together form a double bonded O or S.
Within this genus are the compounds wherein:
$R^1$ is selected from the group consisting of
  (a) $S(O)_2CH_3$,
  (b) $S(O)_2NH_2$,
  (c) $S(O)(NH)NH_2$,
$R^2$ is selected from the group consisting of
  mono-, di- or tri-substituted phenyl or naphthyl wherein the substituent is selected from the group consisting of
    (1) hydrogen,
    (2) halo,
    (3) $C_{1-6}$alkoxy,
    (4) $C_{1-4}$alkylthio,
    (5) CN,
    (6) $CF_3$,
    (7) $C_{1-4}$alkyl,
    (8) $N_3$,
    (9) —$CO_2H$,
    (10) —$CO_2$—$C_{1-4}$alkyl,
    (11) —$C(R^5)(R^6)$—OH,
    (12) —$C(R^5)(R^6)$—O—$C_{1-4}$alkyl, and
    (13) —$C_{1-4}$alkyl—$CO_2$—$R^5$;
$R^3$ is $CH_2OR^7$, CN, $CH_2CN$, or $C_{1-6}$fluoroalkyl;
$R^4$ is
  (a) substituted phenyl or substituted heteroaryl, said substituents are selected from the group consisting of (1) hydrogen,
(2) fluoro, chloro and bromo,
(3) $C_{1-4}$alkyl,
(4) $C_{1-4}$alkoxy,
(5) $C_{1-4}$alkylthio,
(6) CN,
(7) $CF_3$, or (b) $C_{1-4}$alkyl, $CH_2OR^7$, CN, $CH_2CN$, or $C_{1-4}$fluoroalkyl; or $R^3$ and $R^4$ together with the carbon to which they are attached form a saturated monocyclic ring of 3, 4, 5, 6 or 7 atoms, optionally containing 1 or 2 heteroatoms chosen independently from O, S, N, and optionally substituted by tri-$R^{12}$, each $R^{12}$ is independently selected from the group consisting of (a) hydrogen,
(b) $C_{1-4}$alkyl,
(c) phenyl or monosubstituted phenyl wherein the substituents may be halo, $C_{1-4}$alkyl, $C_{1-4}$alkoxy, $C_{1-6}$alkylthio, CN, or $CF_3$,
(d) benzyl or monosubstituted benzyl wherein the substituents may be halo, $C_{1-4}$alkyl, $C_{1-4}$alkoxy, $C_{1-4}$alkylthio, CN, or $CF_3$,
(e) —$CO_2$—$C_{1-4}$alkyl,
(f) halo, $R^5$, $R^6$ and $R^7$ are each independently selected from the group consisting of
(a) hydrogen, and
(b) $C_{1-4}$alkyl,
or $R^5$ and $R^6$ together with the carbon to which they are attached form a saturated monocyclic carbon ring of 3, 4, 5, 6 or 7 atoms;

$R^{10}$ and $R^{11}$ are independently
(a) hydrogen,
(b) substituted phenyl or substituted heteroaryl, said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(c) $C_{1-4}$alkyl, $CH_2OR^7$, CN, $CH_2CN$, or $C_{1-4}$fluoroalkyl; or $R^{10}$ and $R^{11}$ together with the carbon to which they are attached form a saturated monocyclic carbon ring of 3, 4, 5, 6 or 7 atoms;

$R^{13}$ and $R^{14}$ are independently selected from the group consisting of:
(a) hydrogen,
(b) $C_{1-4}$alkyl.

The invention is illustrated by the compounds of Examples 1 through 14 as disclosed herein as well as the compounds of Table I through IV.

For purposes of this specification, alkyl is defined to include linear, branched, and cyclic structures, with $C_{1-6}$alkyl including, but not restricted to, methyl, ethyl, propyl, 2-propyl, n-, i-, s- and t-butyl, pentyl, hexyl, 1,1-dimethylethyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$alkylthio is intended to include alkylthio groups of from 1 to 6 carbon atoms of a straight, branched or cyclic configuration. Examples of lower alkylthio groups include methylthio, n-propylthio, isopropylthio, cyclohexylthio, etc. By way of illustration, the propylthio group signifies —$SCH_2CH_2CH_3$. $C_{1-6}$fluoroalkyl includes alkyl groups of from 1 to 6 carbon atoms of a straight, branched or cyclic configuration, in which one or more hydrogen is replaced by fluorine. Examples are —$CHF_2$, $CH_2F$, —$CF_3$, —$CH_2CF_3$, c-pr-$F_5$, c-Hex-$F_{11}$, and the like. Halo includes F, Cl, Br, or I. Heteroaryl includes furan, thiophene, pyrrole, isoxazole, isothiazole, pyrazole, oxazole, thiazole, imidazole, 1,2,3-oxadiazole, 1,2,3-thiadiazole, 1,2,3-triazole, 1,3,4-oxadiazole, 1,3,4-thiadiazole, 1,3,4-triazole, 1,2,5-oxadiazole, 1,2,5-thiadiazole, pyridine, pyridazine, pyrimidine, pyrazine, 1,2,4-triazine, 1,3,5-triazine, 1,2,4,5-tetrazine, and the like.

Exemplifying the invention are:

(a) 5,5-Dimethyl-4-(4-(methylsulfonyl)phenyl)-3-(4-methoxyphenyl)-2-(5H)-furanone,
(b) 5,5-Dimethyl-3-(3-methoxyphenyl)-4-(4-(methylsulfonyl)phenyl)-2-(5H)-furanone,
(c) 5,5-Dimethyl-3-(4-isopropylphenyl)-4-(4-(methylsulfonyl)phenyl)-2-(5H)-furanone,
(d) 5,5-Dimethyl-4-(4-(methylsulfonyl)phenyl)-3-phenyl-2-(5H)-furanone,
(e) 3-(Benzo[1,3]dioxol-5-yl)-5,5-dimethyl-4-(4-(methylsulfonyl)phenyl)-2-(5H)-furanone,
(f) 5,5-Dimethyl-3-(4-methylphenyl)-4-(4-(methylsulfonyl)phenyl)-2-(5H)-furanone,
(g) 5,5-Dimethyl-4-(4-(methylsulfonyl)phenyl)-3-(4-trifluoromethylphenyl)-2-(5H)-furanone,
(h) 5,5-Dimethyl-3-(3-methylphenyl)-4-(4-(methylsulfonyl)phenyl)-2-(5H)-furanone,
(i) 5,5-Dimethyl-3-cyclohexyl-4-(4-(methylsulfonyl)phenyl)-2-(5H)-furanone,
(j) 4-(4-(Methylsulfonyl)phenyl)-3-phenyl-1-oxa-spiro[4,4]non-3-en-2-one,
(k) 5,5-Dimethyl-3-(4-(methylsulfonyl)phenyl)-2-phenylocyclopent-2-enone,
(l) 4,4-Dimethyl-3-(4-(methylsulfonyl)phenyl)-2-phenylcyclopent-2-enone,
(m) 7-(4-(methylsulfonyl)phenyl)-6-phenyl-4-oxa-spiro[2.4]-hept-6-en-5-one, and
(n) 5,5-Bis(fluoromethyl)-3-phenyl-4-(4-(methylsulfonyl)phenyl)-2-(5H)-furanone.

Also exemplifying the invention are the compounds of Examples 15–41.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of compound of formula I as described above.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of compound of formula I as described above.

In a third embodiment, the invention encompasses a method of inhibiting cyclooxygenase and treating cyclooxygenase mediated diseases, advantageously treated by an active agent that selectively inhibits COX-2 in preference to COX-1 as disclosed herein comprising: administration to a patient in need of such treatment of a non-toxic therapeutically effective amount of a compound of Formula I as disclosed herein.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease, and for the prevention of bone loss (treatment of osteoporosis).

By virtue of its high cyclooxygenase-2 (COX-2) activity and/or its specificity for cyclooxygenase-2 over cyclooxygenase-1 (COX-1), Compound I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxy-ethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods.

Method A

Friedel-Crafts-type acylation of thioanisole with an appropriate acid chloride provides ketone 1. A mixture of 1, an aqueous base such as NaOH, an organic solvent such as $CCl_4$/toluene and a phase transfer catalyst such as Aliquat 333™ is stirred in air at room temperature to provide 2. Acylation of 2 with an appropriately substituted aryl acetic acid chloride in the presence a base such as pyridine followed by treatment with DBU affords lactone 3. Oxidation of 3 with OXONE™ or a peracid such as MMPP yields the final product 4 ($R_a$=Me). Alternatively, compound 2 can be oxidized with OXONE™ or a peracid such as MMPP to its corresponding sulfone 5 ($R_a$=Me), which can then be acylated and cyclized under the same conditions as described for 2 to give the final product 4. By methods known in the art, the —SMe group of 2 or 3 can be converted to the —$SO_2NH_2$ group.

METHOD A

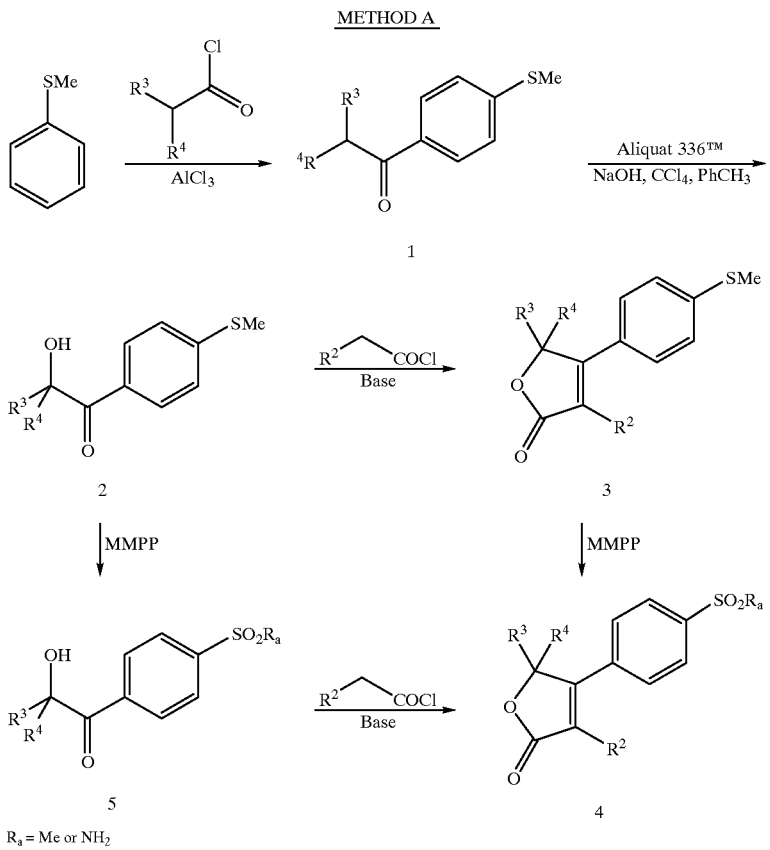

Method B

Reaction of a 4,4-disubstituted-2-cyclopenten-1-one with iodine in pyridine and an inert solvent provides iodide 6, which can be coupled with an appropriately substituted aryl boronic acid in the presence of a Pd° catalyst to give enone 7. Addition of 4-methylthiophenyllithium to 7 affords allylic alcohol 8, which, upon oxidation with PCC or PDC, can be transformed to enone 9. Oxidation of 9 with OXONE™ or a peracid such as MMPP provides the desired product 10. "Ar" is as defined for $R^2$ (c) and (d).

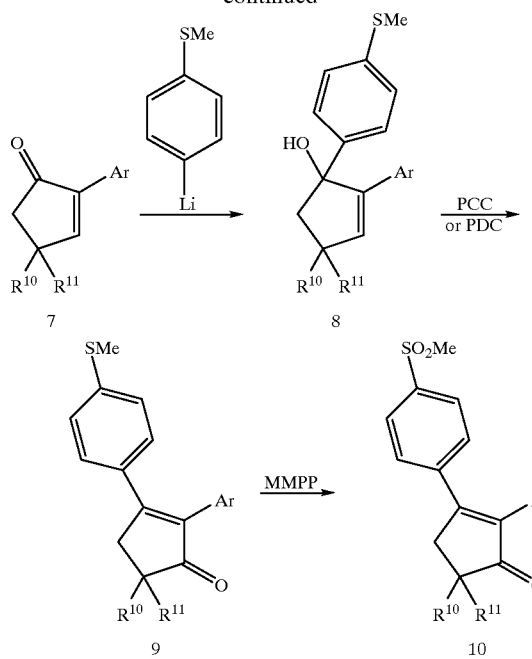

METHOD B

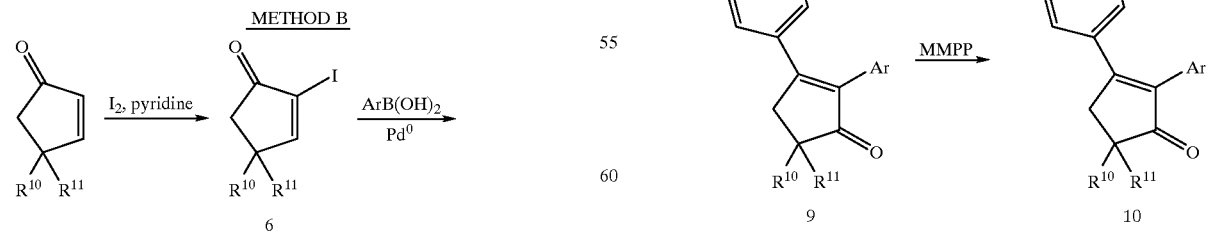

Method C 2,2-Disubstituted pent-4-enal (prepared by the method described by P. D. Magnus and M. S. Nobbs, Syn. Comm. 1980, 10, 273) is reacted with an appropriate organometallic reagent to provide alcohol 11, which can then be oxidized to ketone 12. Ketone 12 is subjected to ozonolysis, followed by treatment with a base such as DBU, to afford cyclic enone 13. Addition of 4-methylthiophenyllithium to 13 gives allylic alcohol 14. Oxidation of 14 with MMPP introduces the required methylsulfonyl group in 15. Oxidation of 15 with PCC affords the final product 16. "Ar" in Method C is as defined for $R^2$ (c) and (d).

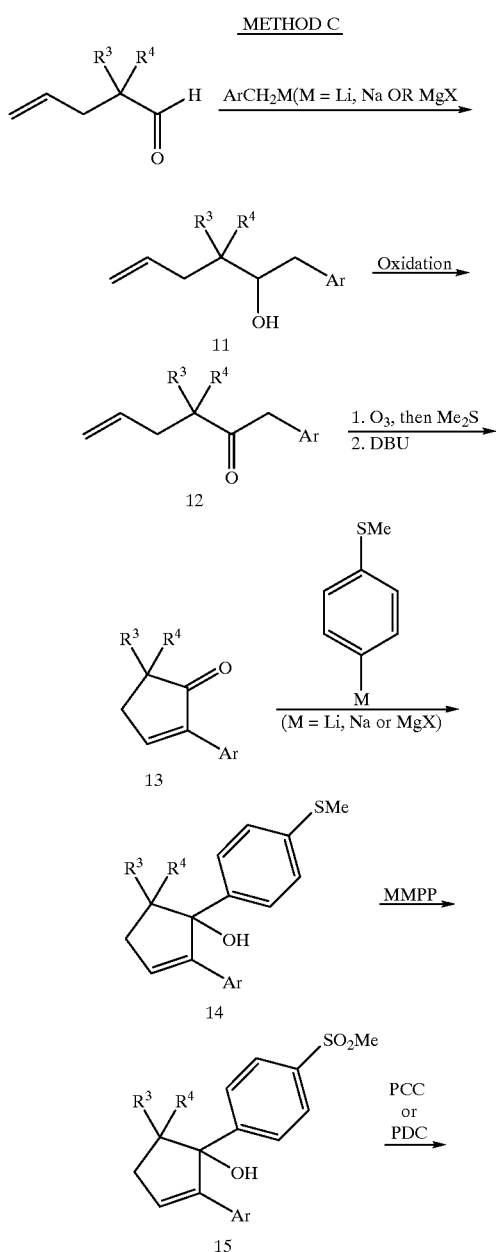

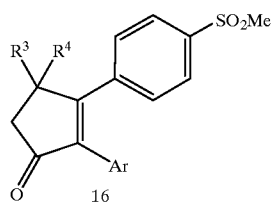

Method D

An appropriately substituted phenyl bromomethyl ketone 17 is reacted with an appropriately substituted acetic acid in a solvent such as acetonitrile in the presence of a base such as triethylamine and then treated with DBU to afford lactone 18. Lactone 18 is reacted with an excess of aqueous formaldehyde solution in the presence of a base such as $K_2CO_3$ in an inert solvent to provide a mixture of alcohols 19 and 20, which are separated by silica gel chromatography. Alcohol 19 is then treated with methanesulfonyl chloride and a base to yield compound 21. Cyclopropanation of 21 with $R^{12}_2CN_2$ can be accomplished using a palladium or rhodium catalyst or with $R^{12}_2CHX$ and a base to afford the desired product 22.

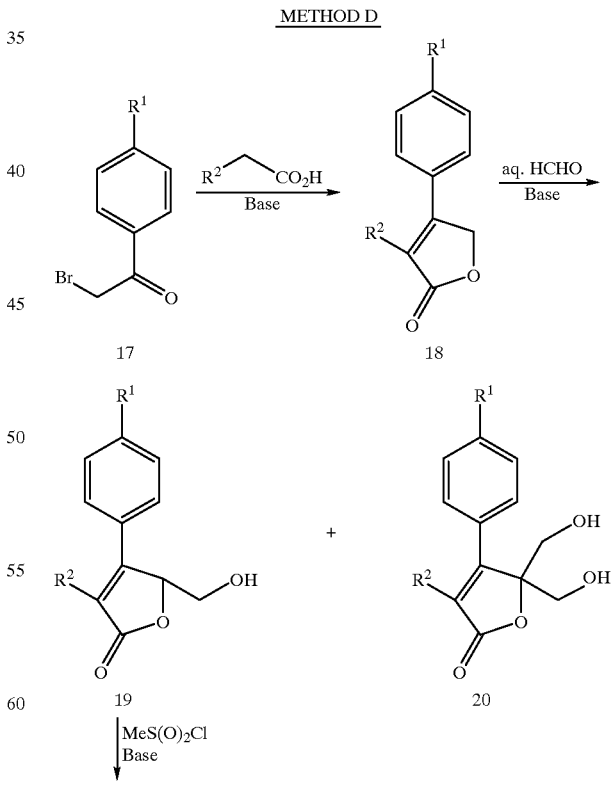

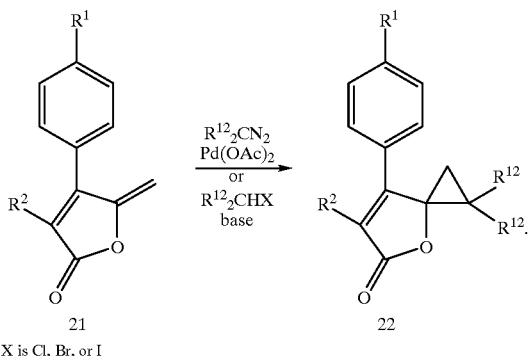

X is Cl, Br, or I

Method E

The diol 20, obtained in Method D, is treated with excess Et$_2$NSF$_3$ in an inert solvent such as CH$_2$Cl$_2$ to provide the desired product 23.

METHOD E

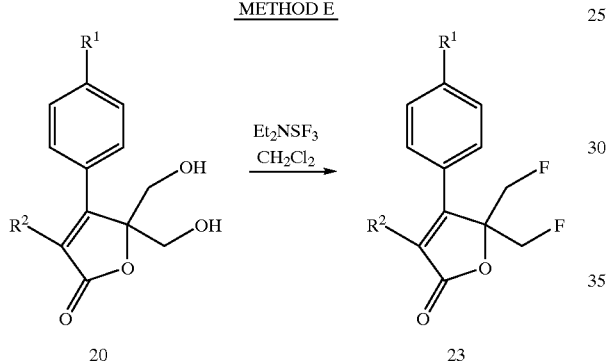

Method F

Arylmethyl ether 24, obtained in Method A, may be demethylated by treatment with BBr$_3$. Treatment of the resulting phenol 26 with NaH in DMF followed by treatment with methyl bromoacetate provides ester 26, which may be hydrolized under alkaline conditions to provide acid 27. Friedel-Crafts cyclization of 27 in PPA provides cyclic ketone 28. This ketone may be alkylated by enolization with LDA followed by quenching with electrophile R$^5$—X. This process may be repeated with electrophile R$^6$—X to provide a mono- or di-alkylated ketone 29.

METHOD F

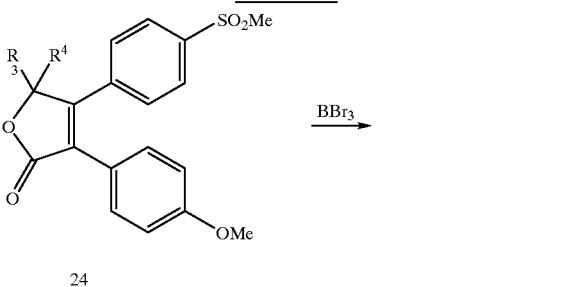

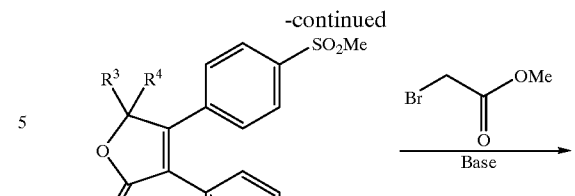

Method G

Phenol 25 may be treated with NaH in DMF and then alkylated with an allylic bromide to give ether 30. Claisen rearrangement of 30 under thermal conditions gives ortho-allyl phenol 31. Oxidation of the double bond in 31 with OsO$_4$/NMO followed by cleavage with NaIO$_4$ provides the lactol 32. Jones oxidation then provides lactone 33.

METHOD G
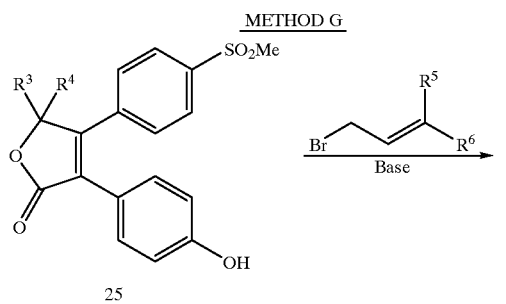
25
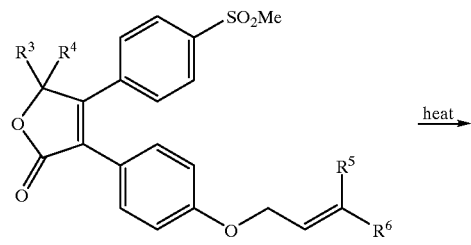
30
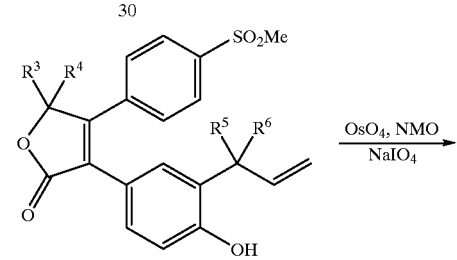
31
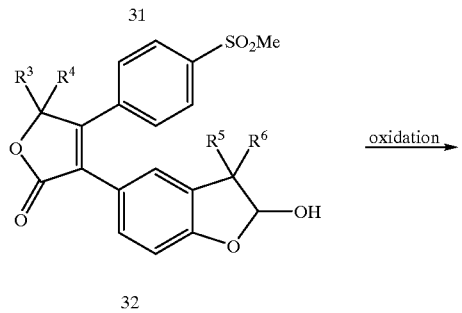
32
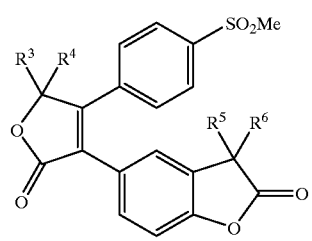
33
Method H
Acid 27 is transformed to acid chloride 34 by treatment with oxalyl chloride in the presence of catalytic DMF. Treatment of 35 with two types of Grignard reagent, $R^5MgX$ and $R^6MgX$, gives tertiary alcohol 35. Cyclization of 35 with a Lewis acid then provides ether 36.
METHOD H
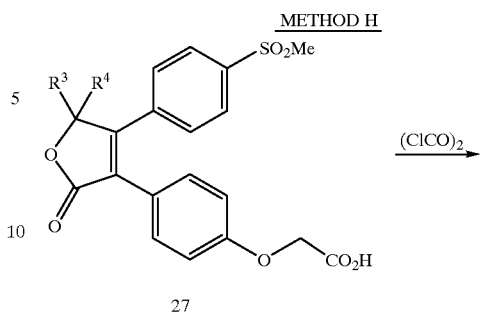
27
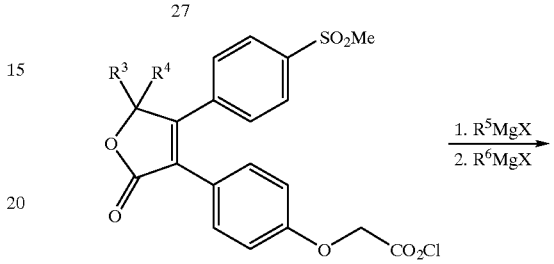
34
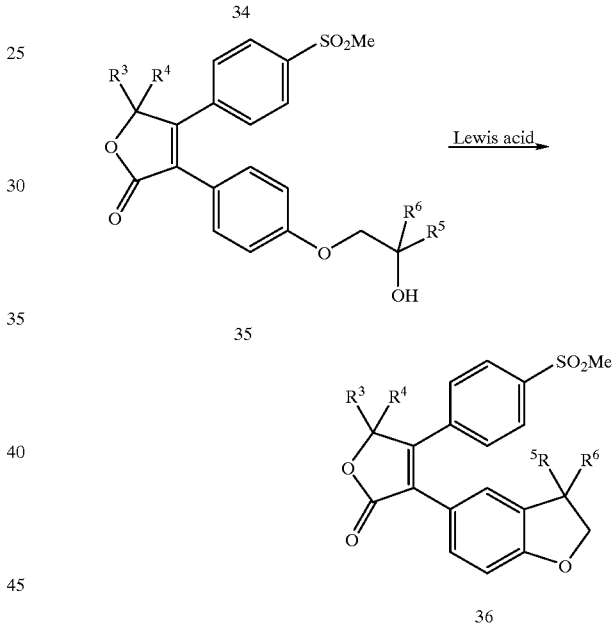
35
36
Method I
Lactol 32 may be treated with $Et_3SiH$ in TFA to provide cyclic ether 36.
METHOD I
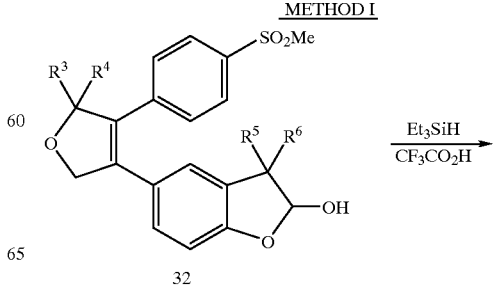
32

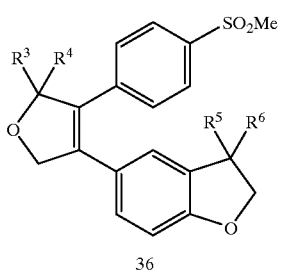

36

Method J

Olefin 31 may be hydroborated with (Sia)$_2$BH followed by peroxide oxidation to give terminal alcohol 37. Jones oxidation accompanied by lactonization provides lactone 38.

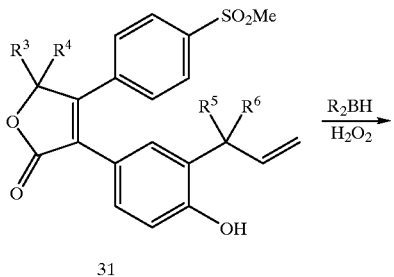

31

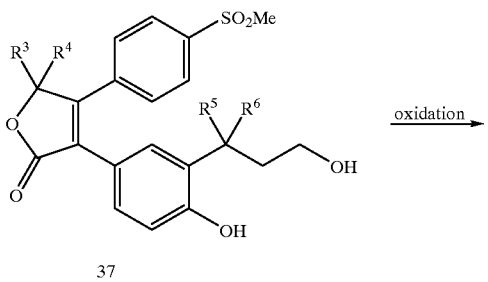

37

38

Method K

A mixture of phenol 25 and an alkyl or benzylic halide R—X in DMF may be treated with NaH to give ether 39.

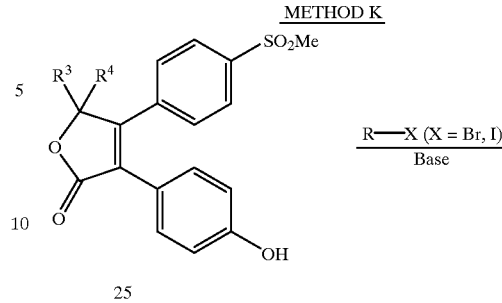

25

39

(R = alkyl, cycloalkyl or benzyl)

Method L

An arylhalide or aryl triflate 40 may be treated with a vinyl boronate or a trialkylstannylacetylene in the presence of Pd° catalyst to provide the corresponding vinylic or acetylenic aromatics 41.

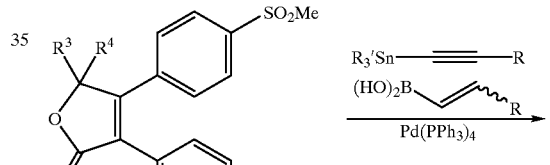

40

41

(X = Br, I or OTf; R = alkyl, cycloalkyl or aryl)

Method M

δ-Valerolactam may be treated with NaH in DMF in the presence of methyl bromoacetate to give ester 42. This is hydrolized under basic conditions to give acid 43 which can be coupled with alcohol 5 under DCC/DMAP conditions to give ester 44. Treatment with NaH gives lactone 45 which, when treated with excess LiAlH₄ gives aminodiol 46. Oxidation of 46 then provides amino lactone 47.

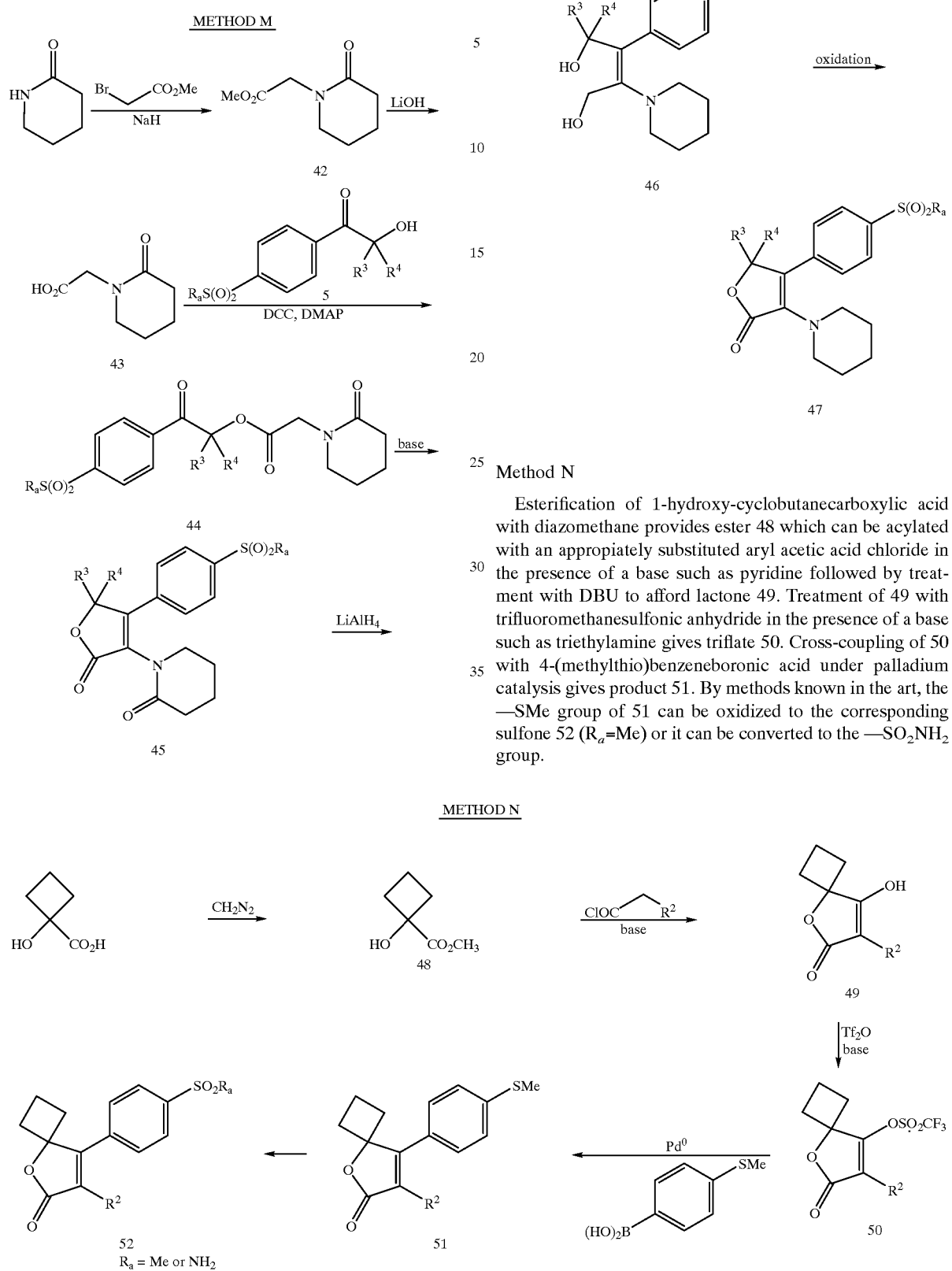

Method N

Esterification of 1-hydroxy-cyclobutanecarboxylic acid with diazomethane provides ester 48 which can be acylated with an appropiately substituted aryl acetic acid chloride in the presence of a base such as pyridine followed by treatment with DBU to afford lactone 49. Treatment of 49 with trifluoromethanesulfonic anhydride in the presence of a base such as triethylamine gives triflate 50. Cross-coupling of 50 with 4-(methylthio)benzeneboronic acid under palladium catalysis gives product 51. By methods known in the art, the —SMe group of 51 can be oxidized to the corresponding sulfone 52 ($R_a$=Me) or it can be converted to the —SO₂NH₂ group.

Representative Compounds

Tables I and II illustrate novel compounds of the present invention. Tables III and IV illustrate compounds of formula I, which are representative of the present invention.

TABLE I

| Structure | Example | Method |
|---|---|---|
| 4-(4-methoxyphenyl)-3-(4-(methylsulfonyl)phenyl)-5,5-dimethylfuran-2(5H)-one | 1 | A |
| 4-(3-methoxyphenyl)-3-(4-(methylsulfonyl)phenyl)-5,5-dimethylfuran-2(5H)-one | 2 | A |
| 4-(4-isopropylphenyl)-3-(4-(methylsulfonyl)phenyl)-5,5-dimethylfuran-2(5H)-one | 3 | A |
| 4-phenyl-3-(4-(methylsulfonyl)phenyl)-5,5-dimethylfuran-2(5H)-one | 4 | A |
| 4-(benzo[d][1,3]dioxol-5-yl)-3-(4-(methylsulfonyl)phenyl)-5,5-dimethylfuran-2(5H)-one | 5 | A |

TABLE I-continued

| Structure | Example | Method |
|---|---|---|
| 4-(4-methylphenyl)-3-(4-(methylsulfonyl)phenyl)-5,5-dimethylfuran-2(5H)-one | 6 | A |
| 4-(4-trifluoromethylphenyl)-3-(4-(methylsulfonyl)phenyl)-5,5-dimethylfuran-2(5H)-one | 7 | A |
| 4-(3-methylphenyl)-3-(4-(methylsulfonyl)phenyl)-5,5-dimethylfuran-2(5H)-one | 8 | A |
| 4-cyclohexyl-3-(4-(methylsulfonyl)phenyl)-5,5-dimethylfuran-2(5H)-one | 9 | A |
| 4-(4-sulfamoylphenyl)-3-(4-(cyclohexyloxy)phenyl)-5,5-dimethylfuran-2(5H)-one | | K |
| 4-(4-(methylsulfonyl)phenyl)-3-(4-(allyloxy)phenyl)-5,5-dimethylfuran-2(5H)-one | 15 | K |

TABLE I-continued
| | Example | Method |
|---|---|---|
| (structure) | | K |
| (structure) | | |
| (structure) | 16 | A |
TABLE II
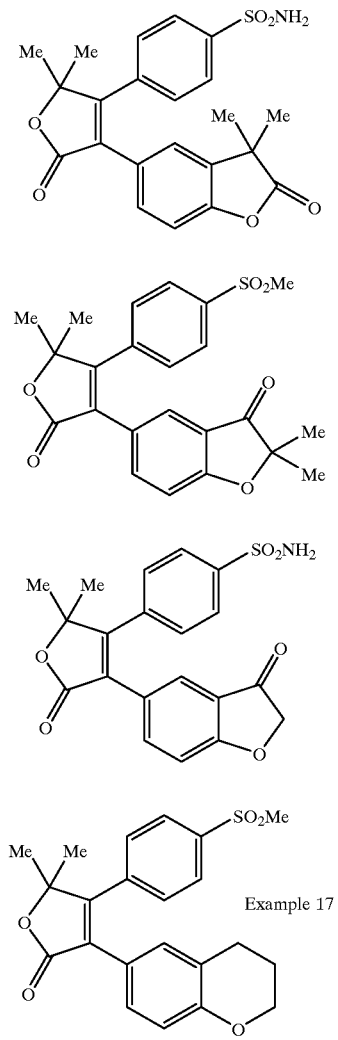

TABLE II-continued
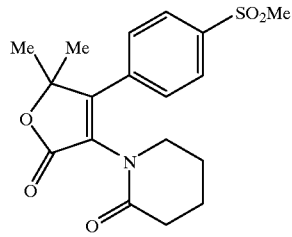
TABLE III
| Example | Method |
|---|---|
| 10 | A |
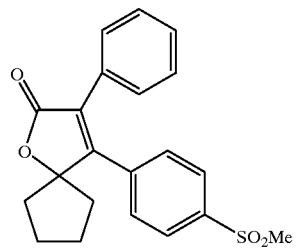
| 11 | B |
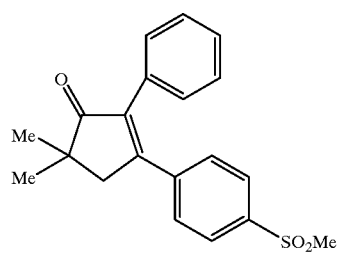
| 12 | C |
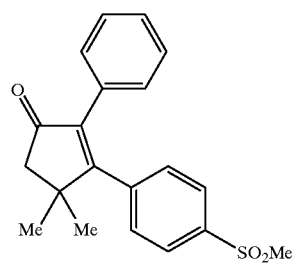
| 13 | D |
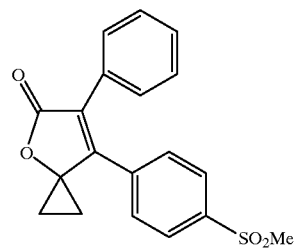
TABLE III-continued
| Example | Method |
|---|---|
| 14 | E |
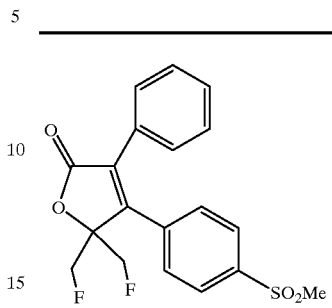
TABLE IV
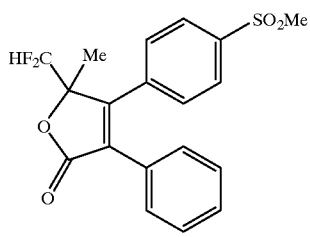
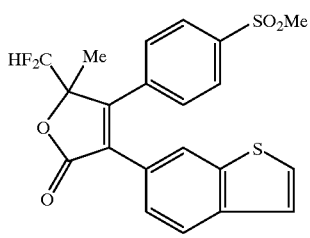
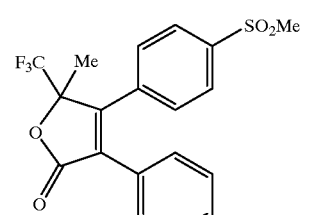
Example 18
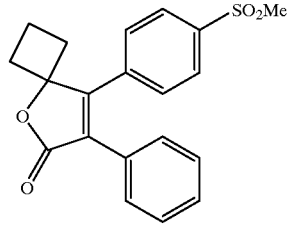
Example 19  Method N TABLE IV-continued
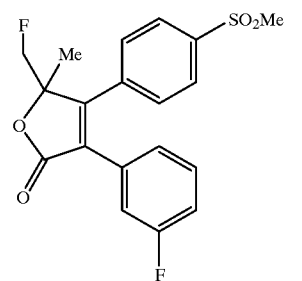
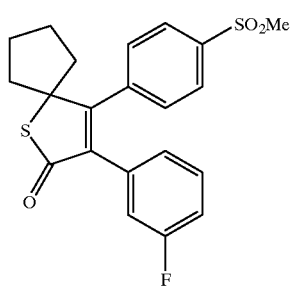
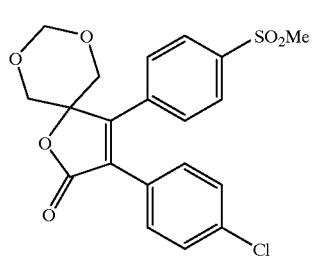
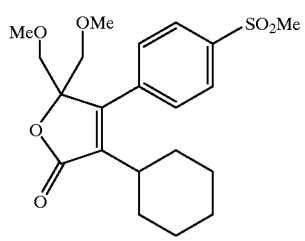
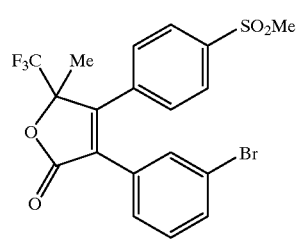
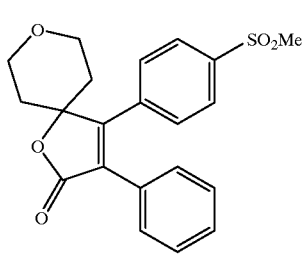
TABLE IV-continued
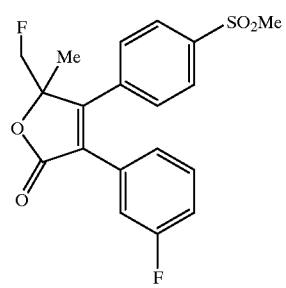
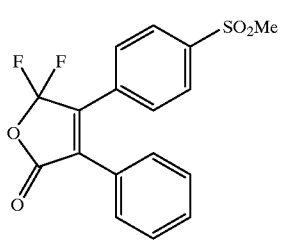
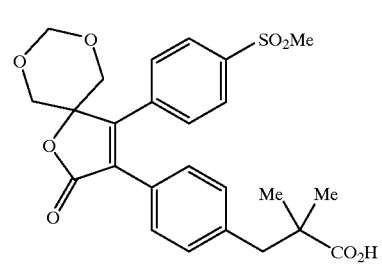
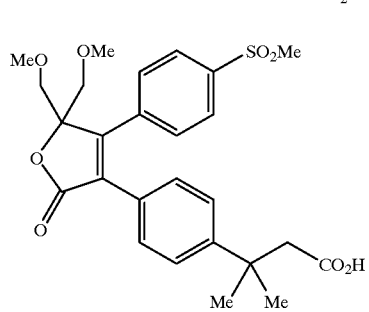
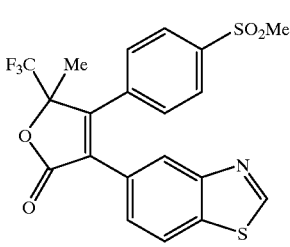
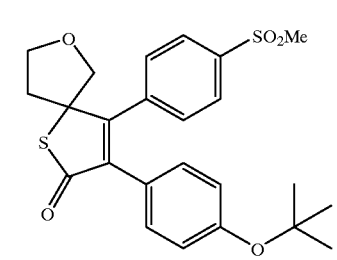

TABLE IV-continued
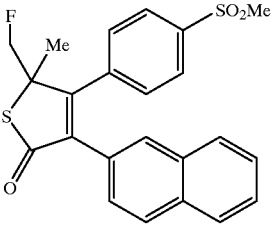
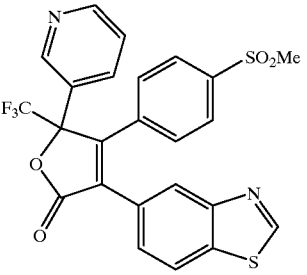
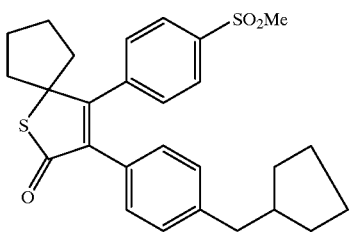
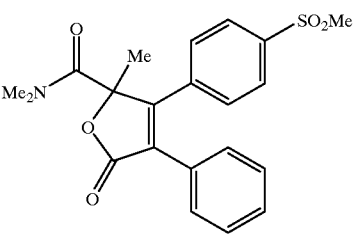
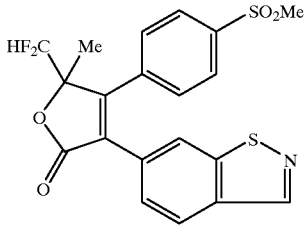
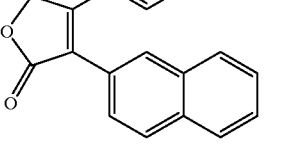
TABLE IV-continued
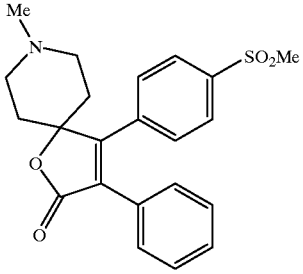
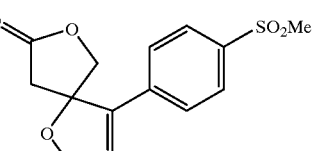
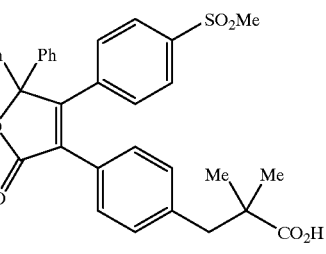
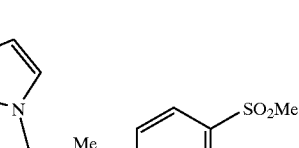
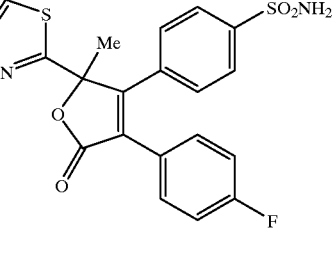

TABLE IV-continued

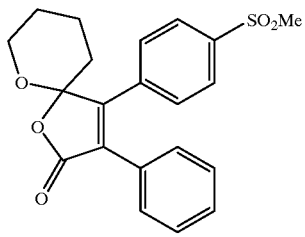

TABLE V

| | Example | Method |
|---|---|---|
| (3-fluorophenyl, SO2Me, cyclopropane spiro lactone) | 20 | N |
| (2-naphthyl, SO2Me, cyclopropane spiro lactone) | 21 | N |
| (2-naphthyl, SO2NH2, cyclopropane spiro lactone) | 22 | N |

TABLE VI

| | Example | Method |
|---|---|---|
| (4-fluorophenyl, SO2Me, cyclobutane spiro lactone) | 23 | N |

TABLE VI-continued

| | Example | Method |
|---|---|---|
| (3-fluorophenyl, SO2Me, cyclobutane spiro lactone) | 24 | N |
| (3,4-difluorophenyl, SO2Me, cyclobutane spiro lactone) | 25 | N |
| (phenyl, SO2NH2, cyclobutane spiro lactone) | 26 | N |
| (4-fluorophenyl, SO2NH2, cyclobutane spiro lactone) | 27 | N |
| (3-fluorophenyl, SO2NH2, cyclobutane spiro lactone) | 28 | N |

TABLE VI-continued
| Example | Method |
|---|---|
| 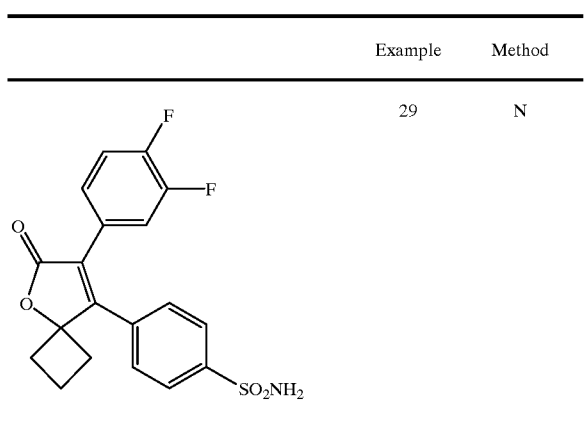 29 | N |
TABLE VII
| Example | Method |
|---|---|
| 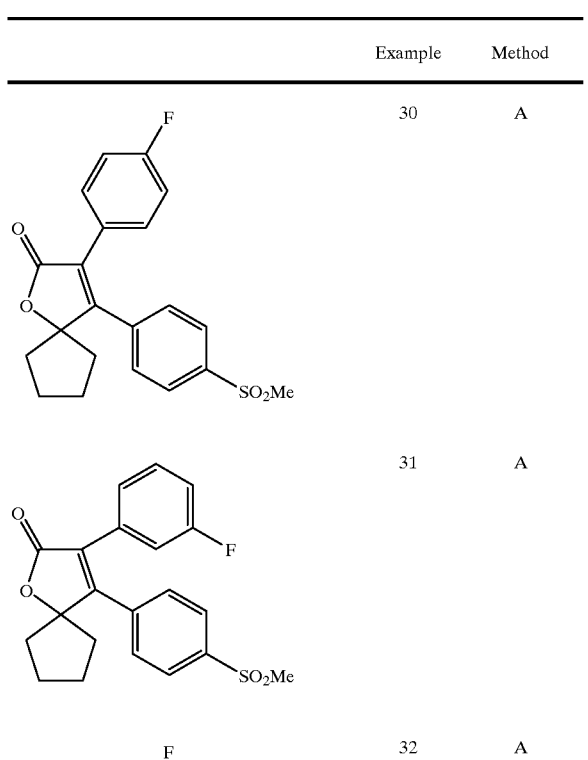 30 | A |
| 31 | A |
| 32 | A |
TABLE VII-continued
| Example | Method |
|---|---|
| 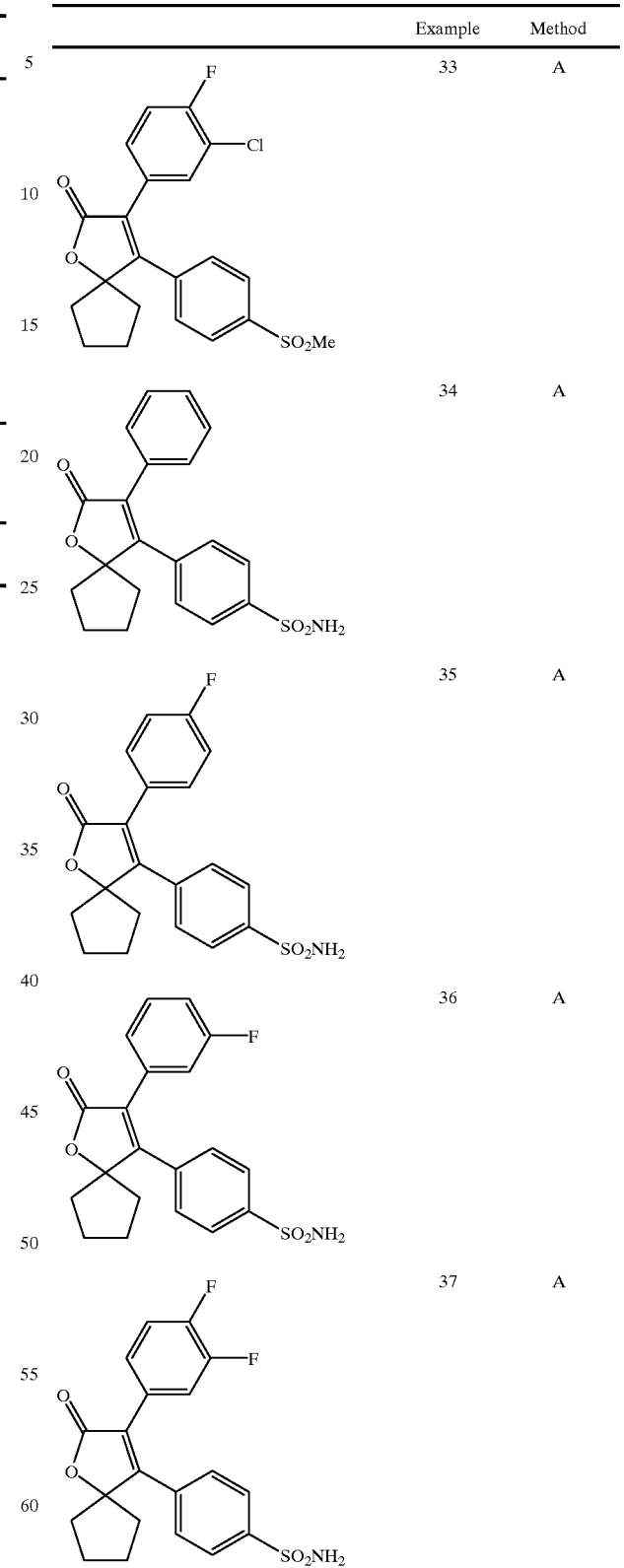 33 | A |
| 34 | A |
| 35 | A |
| 36 | A |
| 37 | A |

TABLE VII-continued

| | Example | Method |
|---|---|---|
| (structure: 3-(4-fluoro-3-chlorophenyl)-4-(4-sulfamoylphenyl)furanone with cyclopentane spiro) | 38 | A |

TABLE VIII

| | Example | Method |
|---|---|---|
| (structure: 3-phenyl-4-(4-methylsulfonylphenyl)furanone with cyclohexane spiro) | 39 | A |
| (structure: 3-phenyl-4-(4-sulfamoylphenyl)furanone with cyclohexane spiro) | 40 | A |
| (structure: 3-(4-fluorophenyl)-4-(4-sulfamoylphenyl)furanone with cyclopentane spiro) | 41 | A |

Assays for Determining Biological Activity

The compound of Formula I can be tested using the following assays to determine their cyclooxygenase-2 inhibiting activity.

Inhibition of Cyclooxygenase Activity

Compounds were tested as inhibitors of cyclooxygenase activity in whole cell cyclooxygenase assays. Both of these assays measured prostaglandin $E_2$ synthesis in response to arachidonic acid, using a radioimmunoassay. Cells used for these assays were human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate.

Assay

For cyclooxygenase assays, osteosarcoma cells are cultured in 1 mL of media in 24-well multidishes (Nunclon) until confluent ($1-2\times10^5$ cells/well). U-937 cells are grown in spinner flasks and resuspended to a final density of $1.5\times10^6$ cells/mL in 24-well multidishes (Nunclon). Following washing and resuspension of osteosarcoma and U-937 cells in 1 mL of HBSS, 1 $\mu$L of a DMSO solution of test compound or DMSO vehicle is added, and samples gently mixed. All assays are performed in triplicate. Samples are then incubated for 5 or 15 minutes at 37° C., prior to the addition of arachidonic acid. Arachidonic acid (peroxide-free, Cayman Chemical) is prepared as a 10 mM stock solution in ethanol and further diluted 10-fold in HBSS. An aliquot of 10 $\mu$L of this diluted solution is added to the cells to give a final arachidonic acid concentration of 10 $\mu$M. Control samples are incubated with ethanol vehicle instead of arachidonic acid. Samples are again gently mixed and incubated for a further 10 min at 37° C. For osteosarcoma cells, reactions are then stopped by the addition of 100 $\mu$L of 1N HCl with mixing and by the rapid removal of the solution from cell monolayers. For U-937 cells, reactions are stopped by the addition of 100 $\mu$L of 1N HCl with mixing. Samples are then neutralized by the addition of 100 $\mu$L of 1N NaOH and $PGE_2$ levels measured by radioimmunoassay.

Rat Paw Edema Assay—Protocol

Male Sprague-Dawley rats (150–200 g) were fasted overnight and were given po either vehicle (1% methocel or 5% Tween 80) or a test compound. One hr later, a line was drawn using a permanent marker at the level above the ankle in one hind paw to define the area of the paw to be monitored. The paw volume ($V_0$) was measured using a plethysmometer (Ugo-Basile, Italy) based on the principle of water displacement. The animals were then injected subplantarly with 50 $\mu$l of 1% carrageenan solution in saline (FMC Corp, Maine) into the paw using an insulin syringe with a 25-gauge needle (i.e. 500 $\mu$g carrageenan per paw). Three hr later, the paw volume ($V_3$) was measured and the increases in paw volume ($V_3$–$V_0$) were calculated. The animals were sacrificed by $CO_2$ aphyxiation and the absence or presence of stomach lesions scored. Data were compared with the vehicle-control values and percent inhibition calculated. Since a maximum of 60–70% inhibition (paw edema) was obtained with standard NSAIDs, $ED_{30}$ values were used for comparison. All treatment groups were coded to eliminate observer bias.

NSAID-Induced Gastrophathy in Rats

Rationale

The major side effect of conventional NSAIDs is their ability to produce gastric lesions in man. This action is believed to be caused by inhibition of COX-1 in the gastrointestinal tract. Rats are particularly sensitive to the actions of NSAIDS. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d.

for 5 days (chronic dosing). Immediately after the administration of the last dose, the rats ate injected via a tail vein with 0.5 mL of $^{51}$Cr-labeled red blood cells from a donor rat. The animals are placed individually in metabolism cages with food and water ad lib. Feces are collected for a 48 h period and $^{51}$Cr fecal excretion is calculated as a percent of total injected dose.

$^{51}$Cr-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 $\mu$Ci of sodium $^{51}$chromate for 30 min at 37° C. At the end of the incubation, the red blood cells are washed twice with 20 mL HBSS to remove free sodium $^5$chromate. The red blood cells are finally reconstituted in 10 mL HBSS and 0.5 mL of the solution (about 20 $\mu$Ci) is injected per rat.

Protein-Losing Gastropathy in Squirrel Monkeys

Rationale

Protein-losing gastropathy (manifested as appearance of cirulating cells and plasma proteins in the GI tract) is a significant and dose-limiting adverse response to standard NSAIDs. This can be quantitatively assessed by intravenous administration of $^{51}$CrCl$_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocel or 5% Tween 80 in H$_2$O vehicles, (3 mL/kg b.i.d.) or test compounds at doses from 1–100 mg/kg b.i.d. for 5 days. Intravenous $^{51}$Cr (5 $\mu$Ci/kg in 1 ml/kg PBS) is administered 1 h after the last drug/vehicle dose, and feces collected for 24 h in a metabolism cage and assessed for excreted $^{51}$Cr by gamma-counting. Venous blood is sampled 1 h and 8 h after the last drug dose, and plasma concentrations of drug measured by RP-HPLC.

Human Whole Blood Assay

Rationale

Human whole blood provides a protein and cell-rich milieu appropriate for the study of biochemical efficacy of anti-inflammatory compounds such as selective Cox-2 inhibitors. Studies have shown that normal human blood does not contain the Cox-2 enzyme. This is consistent with the observation that Cox-2 inhibitors have no effect on PGE$_2$ production in normal blood. These inhibitors are active only after incubation of human whole blood with LPS (lipopolysaccharide), which induces Cox-2. This assay can be used to evaluate the inhibitory effect of selective Cox-2 inhibitors on PGE2 production. As well, platelets in whole blood contain a large amount of the Cox-1 enzyme. Immediately following blood clotting, platelets are activated through a thrombin-mediated mechanism. This reaction results in the production of thromboxane B$_2$ (TxB$_2$) via activation of Cox-1. Thus, the effect of test compounds on TxB$_2$ levels levels following blood clotting can be examined and used as an index for Cox-1 activity. Therefore, the degree of selectivity by the test compound can be determined by measuring the levels of PGE$_2$ after LPS induction (Cox-2) and TxB$_2$ following blood clotting (Cox-1) in the same assay.

Method

A. Cox-2 (LPS-induced PGE$_2$ Production)

Fresh blood was collected in heparinized tubes by venipuncture from both male and female volunteers. The subjects had no apparent inflammatory conditions and had not taken any NSAIDs for at least 7 days prior to blood collection. Plasma was immediately obtained from a 2 mL blood aliquot to use as blank (basal levels of PGE$_2$). The remaining blood was incubated with LPS (100 $\mu$g/ml final concentration, Sigma Chem, #L-2630 from *E. coli;* diluted in 0.1% BSA-Phosphate buffered saline) for 5 minutes at room temperature. Five hundred $\mu$L aliquots of blood were incubated with either 2 $\mu$L vehicle (DMSO) or 2 $\mu$L of a test compound at final concentrations varying from 10 nM to 30 $\mu$M for 24 hours at 37° C. At the end of the incubation, the blood was centrifuged at 12,000×g for 5 minutes to obtain plasma. A 100 $\mu$L aliquot of plasma was mixed with 400 $\mu$L of methanol for protein precipitation. The supernatant was obtained and was assayed for PGE$_2$ using a radioimmunoassay kit (Amersham, RPA#530) after conversion of PGE$_2$ to its methyl oximate derivative according to the manufacturer's procedure.

B. Cox-1 (Clotting-induced TxB$_2$ Production)

Fresh blood was collected into vacutainers containing no anticoagulants. Aliquots of 500 $\mu$L were immediately transferred to siliconized microcentrifuge tubes preloaded with 2 $\mu$L of either DMSO or a test compound at final concentrations varying from 10 nM to 30 $\mu$M. The tubes were vortexed and incubated at 37° C. for 1 hour to allow blood to clot. At the end of incubation, serum was obtained by centrifugation (12,000×g for 5 min.). A 100 $\mu$L aliquot of serum was mixed with 400 $\mu$L of methanol for protein precipitation. The supernatant was obtained and was assayed for TxB$_2$ using a enzyme immunoassay kit (Cayman, #519031) according to the manufacturer's instruction.

Representative Biological Data

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin E$_2$ (PGE$_2$) synthesized in the presence of arachidonic acid, cyclooxygenase-1 or cyclooxygenase-2 and a putative inhibitor. The IC$_{50}$ values represent the concentration of putative inhibitor required to return PGE$_2$ synthesis to 50% of that obtained as compared to the uninhibited control.

The results for inhibition of PGE$_2$ production may be seen in Table V.

TABLE V

| Example | HWB Cox-2 IC$_{50}$ ($\mu$M) | HWB Cox-1 IC$_{50}$ ($\mu$M) | Rat Paw Edema ED$_{30}$ (mg(kg) |
|---|---|---|---|
| 2 | 0.81 | >30 | 0.30 |
| 4 | 0.17 | >30 | 0.26 |
| 10 | 0.37 | 30 | 0.41 |
| 11 | 0.06 | 2.2 | 1.17 |
| 13 | 0.60 | >30 | 0.30 |
| 14 | 1.1 | >30 | 0.62 |

The Following Abbreviations have the Indicated Meanings

Ac=acetyl
AIBN=2.2-azobisisobutyronitrile
Bn=benzyl
DBU=diazabicyclo[5.4.0]undec-7-ene
DCC=1,3-dicyclohexylcarbodiimide
DMAP=4-(dimethylamino)pyridine
DMF=N,N-dimethylformamide
DMSO=dimethyl sulfoxide Et₃N=triethylamine
Fur=furandiyl
HBSS=Hank's balanced salt solution
HWB=human whole blood
KHMDS=potassium hexamethyldisilazane
LDA=lithium diisopropylamide
MMPP=magnesium monoperoxyphthalate
Ms=methanesulfonyl=mesyl
MsO=methanesulfonate=mesylate
NBS=N-bromosuccinimide
NCS=N-chlorosuccinimide
NIS=N-iodosuccinimide
NSAID=non-steroidal anti-inflammatory drug
PCC=pyridinium chlorochromate
PDC=pyridinium dichromate
Ph=phenyl
Phe=benzenediyl
PPA=polyphosphoric acid
Pye=pyridinediyl
r.t.=room temperature
rac.=racemic
Tf=trifluoromethanesulfonyl=triflyl
TFA trifluoroacetic acid
TfO=trifluoromethanesulfonate=triflate
Th=2- or 3-thienyl
THF=tetrahydrofuran
Thi=thiophenediyl
TLC=thin layer chromatography
Ts=p-toluenesulfonyl=tosyl
TsO=p-toluenesulfonate=tosylate
Tz=1H (or 2H)-tetrazol-5-yl
$C_3H_5$=allyl
—$SO_2Me$=methyl sulfone
—$SO_2NH_2$=sulfonamide Alkyl Group Abbreviations Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl The invention will now be illustrated by the following non-limiting examples in which, unless stated otherwise:

(i) all operations were carried out at room or ambient temperature, that is, at a temperature in the range 18–25° C.;

(ii) evaporation of solvent was carried out using a rotary evaporator under reduced pressure (600–4000 pascals: 4.5–30 mm Hg) with a bath temperature of up to 60° C.;

(iii) he course of reactions was followed by thin layer chromatography (TLC) and reaction times are given for illustration only; (iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)).

EXAMPLE 1

5,5-Dimethyl-4-(4-(methylsulfonyl)phenyl)-3-(4-methoxyphenyl)-2-(5H)-furanone

Step 1

2-Methyl-1-(4(methylthio)phenyl)-propan-1-one

To a suspension of aluminum chloride (136 g, 1.02 mol) in chloroform (1.0 L) cooled to −10° C., was added dropwise isobutyrylchloride (115 mL, 1.10 mol). Then thioanisole (100 mL, 0.85 mol) was added dropwise. Upon completion of addition the reaction was allowed to proceed at r.t. for 1.5 h. The reaction was cooled to 10° C. and quenched by addition of water (750 mL). The organic layer was separated, washed with water (2×500 mL), saturated $NaHCO_3$ solution(2×500 mL), brine (1×500 mL), and then dried over $Na_2SO_4$. After concentration in vacuo., the resulting crude product crystallized upon standing under high vacuum for 30 min to give the title compound as a brown solid.

Step 2

2-Hydroxy-2-methyl-1-(4-(methylthio)phenyl)-propan-1-one

To a solution of 2-methyl-1-(4-(methylthio)phenyl)-propan-1-one (28.5 g, 147 mmol, Step 1), Aliquat 336 (11.0 mL, 24 mmol) and carbon tetrachloride (21 mL, 218 mmol) in toluene (43 mL) was added sodium hydroxide (12.9 g, pellets, 322 mmol). The reaction was stirred at 15° C. for 2 h and then at r.t. for 16 h. The reaction was diluted with water (100 mL), brine (100 mL) and EtOAc (300 mL). The aqueous phase was acidified with 1 N HCl and extracted with EtOAc (100 mL). The combined organic layers were dried over $Na_2SO_4$ and concentrated. The crude product was purified by silica gel chromatography eluted with 15% EtOAc in hexane to give the title compound as a thick syrup.

Step 3

2-Hydroxy-2-methyl-1-(4-methylsulfonylphenyl)-propan-1-one

To a cold (4° C.) solution of 2-hydroxy-2-methyl-1-(4-(methylthio)phenyl)-propan-1-one (45.0 g, 214 mmol, Step 2) in t-butanol (500 mL) and $CH_2Cl_2$ (500 mL) was added a solution of OXONE™ (194 g, 316 mmol) in water (1.4 L). The resulting suspension was stirred at r.t. for 18 h. The reaction was diluted with EtOAc (400 mL) and the layers were separated. The aqueous layer was extracted with EtOAc (2×250 mL). The combined organic layers were dried over $Na_2SO_4$ and concentrated in vacuo. The crude product was dissolved in diethyl ether (250 mL), hexane was added (150 mL) and the product was swished for 2 h. The product was collected by filtration to give the title compound as a yellow solid.
Step 4

5,5-Dimethyl-4-(4-(methylsulfonyl)phenyl)-3-(4-methoxyphenyl)-2-(5H)-furanone To a cold solution (0° C.) of 2-hydroxy-2-methyl-1-(4-(methylsulfonyl)phenyl)-propane-1-one (726 mg, 3.5 mmol, Step 3), pyridine (0.5 mL, 6.2 mmol) in $CH_2Cl_2$ (10 mL) was added 4-methoxyphenylacetyl chloride (1.5 g, 8.4 mmol) over 2 minutes. The resulting yellow solution was stirred at r.t. for 18 h. Then DBU was added in portions every 30 min. (3×1.0 mL, 3×6.7 mmol). The reaction was diluted with EtOAc (100 mL) and 1N HCl (50 mL). The organic layer was washed with water (50 mL), dried over $MgSO_4$ and concentrated. The crude product was purified first by flash chromatography eluted with 40% EtOAc in hexane and then by crystallization in EtOAc and hexane (1:1, 26 mL) to give the title compound as a white solid.

$^1$H NMR (400 MHz, $CD_3COCD_3$) 1.60 (s, 6H), 3.18 (s, 3H), 3.76 (s, 3H), 6.83 (dt, 2H), 7.32 (dt, 2H), 7.65 (dt, 2H), 8.05 (dt, 2H), m.p. 148° C.

EXAMPLE 2

5,5-Dimethyl-3-(3-methoxyphenyl)-4-(4-(methylsulfonyl)phenyl)-2-(5H)-furanone $^1$H NMR ($d_6$-acetone, 400 MHz): δ1.62 (6H, s), 3.17 (3H, s), 3.61 (3H, s), 6.85 (1H, dt), 6.91 (1H, dd), 6.96 (1H, dt), 7.18 (1H, t), 7.68 (2H, dm), 8.05 (2H, dm).

EXAMPLE 3

5,5-Dimethyl-3-(4-isopropylphenyl)-4-(4-(methylsulfonyl)phenyl)-2-(5H)-furanone $^1$H NMR ($d_6$-acetone, 400 MHz): δ1.17 (6H, d), 1.60 (6H, s), 2.90 (1H, m), 3.18 (3H, s), 7.15 (2H, d), 7.32 (2H, d), 7.67 (2H, d), 8.05 (2H, d).

EXAMPLE 4

5,5-Dimethyl-4-(4-(methylsulfonyl)phenyl)-3-phenyl-2-(5H)-furanone

Analysis calculated for $C_{19}H_{18}O_4S$ C, 66.65; H, 5.30; S, 9.36.
Found C, 66.36; H, 5.32; S, 9.48.
m.p. 159° C.

EXAMPLE 5

3-Benzo[1,3]-dioxol-5-yl-5,5-dimethyl-4-(4-(methylsulfonyl)-phenyl)2-(5H)-furanone Analysis calculated for $C_{20}H_{18}O_6S$ C, 62.17; H, 4.70.
Found C, 62.52; H, 4.82.

EXAMPLE 6

5,5-Dimethyl-3-(4-methylphenyl)-4-(4-(methylsulfonyl)phenyl)-2-(5H)-furanone m.p. 108–109° C.
M.S. (DCI, $CH_4$) calculated for M$^+$: 356 Found for M$^+$+1: 357.

EXAMPLE 7

5,5-Dimethyl-4-(4-(methylsulfonyl)phenyl)-3-(4-trifluoromethylphenyl)-2-(5H)-furanone m.p. 155–156° C.

EXAMPLE 8

5,5-Dimethyl-3-(3-methylphenyl)-4-(4-(methylsulfonyl)phenyl)-2-(5H)-furanone m.p. 167–168° C.

EXAMPLE 9

5,5-Dimethyl-3-cyclohexyl-4-(4-(methylsulfonyl)phenyl)-2-(5H)-furanone

Step 1

Cyclohexylacetyl chloride

To a 0° C. solution of cyclohexaneacetic acid (2.12 g, 14.9 mmol) in 30 mL of $CH_2Cl_2$ was added two drops of DMF followed by oxalyl chloride (1.3 mL, 14.9 mmol). The solution was warmed to r.t. and stirred overnight. The solvent was remove in vacuo to give 1.60 g of the title compound as a colourless liquid.

$^1$H NMR ($d_6$-acetone, 300 MHz): 2.78 (d, 2H), 1.92 (m, 1H), 1.85–1.60 (m, 5H), 1.40–0.95 (m, 5H).
Step 2

Cyclohexylacetic acid, 1,1-dimethyl-2-((4-methylsulfonyl)-phenyl)-2-oxo-ethyl ester To a 0° C. solution of the alcohol from Example 1, Step 3 in 15 mL $CH_2Cl_2$ was added pyridine (0.35 mL, 4.3 mmol). A solution of cyclohexylacetyl chloride (473 mg, 1.95 mmol) in 5 mL $CH_2Cl_2$ was then added via cannula. A small amount of DMAP was added, and the solution was stirred overnight at r.t. The mixture was diluted with $CH_2Cl_2$ and washed successively with 1M NaOH, 1M HCl and brine, filtered through cotton and evaporated. Purification by chromatogrphy (30% EtOAc/hexanes) provided 504 mg of the title ester.

$^1$H NMR ($d_6$-acetone, 300 MHz): 8.20 (m, 2H), 8.04 (m, 2H), 3.14 (s, 3H), 2.12 (d, 2H), 1.70 (s, 6H), 1.57 (m, 3H), 1.40 (m, 2H), 1.12 (m, 4H), 0.80 (m, 2H).
Step 3

5,5-Dimethyl-3-cyclohexyl-4-(4-(methylsulfonyl)phenyl)-2-(5H)-furanone

To a 0° C. solution of 500 mg (1.36 mmol) of cyclohexylacetic acid, 1,1-dimethyl-2-((4-methylsulfonyl)-phenyl)-2-oxo-ethyl ester in 25 ml DMF was added 157 mg (3.92 mmol) of hexane-washed 60% NaH dispersion. Stirred 5 h, allowing the solution to warm to room temperature, then quenched with 1M HCl. Partitioned between 1:1 EtOAc/ether and $H_2O$. The organic layer was washed with $H_2O$, brine and dried over $Na_2SO_4$. Purification by chromatography (40→50% EtOAc/hexanes) gave 160 mg (34%) of the title compound as an oil.

$^1$H NMR (d$_6$-acetone, 300 MHz): 8.09 (m, 2H), 7.62 (m, 2H), 3.20 (s, 3H), 2.18 (m, 1H), 1.75–1.55 (m, 6H), 1.47 (s, 6H), 1.30–1.05 (m, 4H).

EXAMPLE 10

4-(4-(Methylsulfonyl)phenyl)-3-phenyl-1-oxa-spiro [4,4]non-3-en-2-one

Step 1

Cyclopentyl-(4-(methylthio)phenyl)-methanone

To a suspension of anhydrous aluminum chloride (9.3 g, 69.6 mmol) in 58 mL CHCl$_3$ at 0° C. was added dropwise cyclopentanecarbonyl chloride (10.0 g, 75.4 mmol), followed by thioanisole (7.21 g, 58.0 mmol). The ice bath was removed and the mixture was stirred at room temperature for 2 h. Water (200 ml) was added with cooling, the layers were separated and the aqueous layer was extracted with CHCl$_3$ (3×50 mL). The combined aqueous layers were dried over MgSO$_4$, filtered and concentrated. The residue was chromatographed on silica gel (4% EtOAc/hexane) to give 11.9 g of the title ketone (93%).

$^1$H NMR (acetone-d$_6$, 400 MHz) 7.94 (d, 2H, J=8.7 Hz), 7.36 (d, 2H, J=8.7 Hz), 3.79 (q, 1H), 2.56 (s, 3H), 2.00–1.71 (m, 4H), 1.70–1.50 (m, 4H).

Step 2

(1-Hydroxycyclopentyl)-(4-(methylthio)phenyl)-methanone

To a solution of the ketone from Step 1 (7.2 g, 32.7 mmol) in 4.7 ml CCl$_4$ and 9.6 ml toluene was added Aliquat 336 (2.11 g, 5.20 mmol) and powdered NaOH (2.88 g, 71.9 mmol) and the mixture was stirred for 16 h at r.t. To the brown mixture was added 100 ml of 5% aq. HCl and extracted with EtOAc (4×100 ml). The combined organic layers were washed with brine, dried over MgSO$_4$, filtered and concentrated. Chromatography on silica gel (20% EtOAc/hexane) gave 5.4 g of the title compound as a white waxy solid (70%).

$^1$H NMR (acetone-d$_6$, 400 MHz) 8.11 (d, 2H, J=8.5 Hz), 7.31 (d, 2H, J=8.5 Hz), 4.63 (s, 1H, disappears by D$_2$O wash), 2.56 (s, 3H), 2.24 (mc, 2H), 1.89 (mc, 4H), 1.71 (mc, 2H).

Step 3

4-(4-(Methylthio)phenyl)-3-phenyl-1-oxa-spiro[4,4] non-3-en-2-one

To the alcohol from Step 2 (924 mg, 3.91 mmol) in 10 mL CH$_2$Cl$_2$ at 0° C. was added pyridine (928 mg, 11.7 mmol) followed by phenylacetyl chloride (1.51 g, 9.77 mmol). The ice bath was removed and the mixture was stirred at room temperature for 15 h. Aq. NH$_4$Cl (100 mL) was added and the mixture was extracted with EtOAc (3×50 mL). The combined organic layers were washed with brine, dried over MgSO$_4$, filtered and concentrated. The residue was dissolved in 16 mL CH$_2$Cl$_2$, DBU (595 mg, 3.91 mmol) was added and the brown solution was stirred at room temperature for 0.5 h. 5% aq. HCl (100 mL) was added and the mixture was extracted with EtOAc (4×50 mL). The combined organic layers were washed with brine, dried over MgSO$_4$, filtered and concentrated to give 1.40 g (quantitative) of the title compound as a yellow solid, used directly in the next step. An analytical sample had mp. 147–148° C. after stirring with Et$_2$O/hexane (2:1).

Step 4

4-(4-(Methylsulfonyl)phenyl)-3-phenyl-1-oxa-spiro [4,4]non-3-en-2-one

The thioether from Step 3 (1.31 g, 3.91 mmol) in 40 mL CH$_2$Cl$_2$ and 10 mL MeOH was cooled in an ice bath. MMPP (2.66 g, 4.30 mmol) was added in two portions. The ice bath was removed and the mixture was stirred for 1 h at room temperature. The suspension was filtered, and the filtrate was washed with saturated aq. NaHCO$_3$, and H$_2$O. After drying over MgSO$_4$ and evaporation of the solvent, a yellow solid was obtained. Stirring this solid with 10 mL of Et$_2$O for 0.5 h and filtration gave 1.48 g of the tide compound as a colorless solid, m.p. 142–143° C.

EXAMPLE 11

5,5-Dimethyl-3-(4-(methylsulfonyl)phenyl)-2-phenylcyclopent-2-enone

Step 1

4,4-Dimethyl-2-iodo-2-cyclopenten-1-one

To a cold (4° C.) solution of iodine (4.5 g, 18 mmol) in carbon tetrachloride (15 mL) and pyridine (15 mL), was added over 1 min. a solution of 4,4-dimethyl-2-cyclopenten-1-one (930 mg, 8.4 mmol) in carbon tetrachloride (15 mL) and pyridine (15 mL). The resulting red-brown solution was stirred at r.t. for 22 h. The reaction was diluted with Et$_2$O (200 mL), washed successively with water (50 mL), 1.0 N HCl (50 mL), water (50 mL), and aqueous Na$_2$S$_2$O$_5$ 20% w/v, then dried over MgSO$_4$ and concentrated in vacuo. The crude product was purified by flash chromatography eluting with 10% EtOAc/hexanes to give the title compound as a white solid.

Step 2

4,4-Dimethyl-2-phenyl-2-cyclopenten-1-one

A 250 mL round bottom flask was charged with 4,4-dimethyl-2-iodo-2-cyclopenten-1-one from Step 1 (1.59 g, 6.7 mmol), bis(benzontrile)-palladium(II) chloride (235 mg, 0.61 mmol), phenylboronic acid (983 mg, 8.1 mmol), triphenylarsine (308 mg, 1.0 mmol), 2.0 M Na$_2$CO$_3$ (8.4 mL, 16.8 mmol) and benzene (70 mL). The reaction flask was well purged with nitrogen and the reaction was stirred at 80° C. for 2.5 h. The reaction was allowed to cool to r.t., diluted with NH$_4$OAc buffer 25% w/v (100 mL) and extracted with EtOAc. The organic extract was dried over MgSO$_4$ and concentrated in vacuo. The crude product was purified by flash chromatography eluting with 10% EtOAc in hexane to give the title compound as a light yellow syrup.

Step 3

4,4-Dimethyl-1-(4-(methylthio)phenyl)-2-phenylcyclopent-2-enol

To a solution of 4-bromothioanisole (2.51 g, 12.3 mmol) in THF (20 mL) at −78° C. was added dropwise a solution of 2.5 M n-butyl lithium in hexane (4.8 mL, 12.0 mmol). The resulting suspension was stirred at this temperature for 1 h and then a solution of 4,4-dimethyl-2-phenyl-2-cyclopenten-1-one from Step 2 (1.25 g, 6.7 mmol) in THF (20 mL) was added slowly via cannula to the cold reaction. The reaction was stirred for 15 min at −78° C. and then for 30 min. at r.t. The reaction was stopped by dilution with NH$_4$OAc buffer 25% w/v and extracted with EtOAc. The organic layer was dried over MgSO$_4$ and concentrated in vacuo. The crude product was purified by flash chromatography eluting with 10% EtOAc/hexanes to give the title compound as a colorless gum.
Step 4

5,5-Dimethyl-3-(4-(methylthio)phenyl)-2-phenolcyclopent-2-enone

To a suspension of 4,4-dimethyl-1-(4-(methylthio) phenyl)-2-phenylcyclopent-2-enol from Step 3 (2.0 g, 6.4 mmol) and powdered 4 Å molecular sieves (2 g) in $CH_2Cl_2$ (50 mL) was added pyridinium chlorochromate (1.6 g, 7.4 mmol). The resulting suspension was vigorously stirred for 18 h. Then powdered 4 Å molecular sieves (2 g) and PCC (1.6 g, 7.4 mmol) were added and the resullting brown suspension was stirred for another 24 h. The reaction was diluted with $CH_2Cl_2$ (100 mL) followed by $Et_2O$ (600 mL) with vigorous stirring for 24 h. The reaction was filtered on a cake of silica gel which was washed with $Et_2O$ (2×100 mL) and the filtrate was concentrated in vacuo. The crude product was purified by flash chromatography eluted with 2% EtOAc in toluene to give the tide compound as a light yellow gum.
Step 5

5,5-Dimethyl-3-(4-(methylsulfonyl)phenyl)-2-phenylocyclopent-2-enone

To a cold solution (4° C.) of 5,5-dimethyl-3-(4-(methylthio)phenyl)-2-phenylcyclopent-2-enone from Step 4 (563 mg, 1.8 mmol) in $CH_2Cl_2$ (16 mL) and in methanol (2 mL) was added monoperoxyphthalic acid, magnesium salt hexahydrate 80% (1.47 g, 2.4 mmol). The resulting suspension was stirred at r.t. for 18 h. The reaction was diluted with EtOAc (150 mL) and a mixture of aq. $NaHCO_3$ sat./water (1:1). The organic layer was dried over $MgSO_4$ and concentrated in vacuo. The crude product was purified first by flash chromatography eluted with 40% of EtOAc/hexanes and then by crystallization in EtOAc/hexanes (1:3, 30 mL) to give the title compound as light yellow needles.

$^1$H NMR (400 MHz, $CD_3COCD_3$) 1.26 (s, 6H), 3.05 (s, 2H), 3.12 (s, 3H), 7.20 (m, 2H), 7.33 (m, 3H), 7.63 (dt, 2H), 7.89 (dt, 2H), m.p. 117° C.

EXAMPLE 12

4,4-Dimethyl-3-(4-(methylsulfonyl)phenyl)-2-phenylcyclopent-2-enone

Step 1

3,3-Dimethyl-1-phenylhex-5-en-2-ol

To a solution of 2,2-dimethylpent-4-enal (11.2 g) in 200 mL of $Et_2O$ cooled to 0° C. was added dropwise a solution of benzylmagnesium chloride (70 mL, 2M in THF). After stirring for 1 h at 0° C., the reaction was quenched with 200 mL of saturated solution of $NH_4Cl$ and the product was extracted with 200 mL of 1:1 EtOAc/hexane. The extract was dried over $Na_2SO_4$ and concentrated. The residue was distilled under reduced pressure to give 16 g of the title compound.
Step 2

3,3-Dimethyl-1-phenylhex-5-en-2-one

To a solution of the product of Step 1 (15 g) and 50 mL of i-$Pr_2NEt$ in 250 mL of $CH_2Cl_2$ cooled at 0° C. was added dropwise a solution of sulfur trioxide pyridine complex (23.8 g) in 100 mL of DMSO. After stirring for 10 min, the reaction mixture was treated with 200 mL $H_2O$ and extracted with 200 mL of 1:1 EtOAc/hexane. The extract was dried over $MgSO_4$ and concentrated to give 15 g of the title compound as a yellow oil.

$^1$H NMR (acetone-$d_6$, 400 MHz) 1.17 (6H, s), 2.36 (2H, dd), 3.87 (2H, s), 5.0–5.15 (2H, m), 5.65–5.80 (1H, m), 7.12–7.30 (5H, m).
Step 3

5,5-Dimethyl-2-phenylcyclopent-2-enone

A solution of the product of Step 2 (15 g) in 70 mL of MeOH and 50 mL of $CH_2Cl_2$ was treated with a stream of ozone/oxygen until the solution turned light blue. Dimethylsulfide (20 mL) was added and the reaction mixture was stirred for 2 h at room temperature and then treated with 5 g of triphenylphosphine for an additional 0.5 h. DBU (1 mL) was then added to the reaction mixture. After stirring for 1 h at room temperature, 1 mL of AcOH was added and the reaction mixture was concentrated. The residue was dissolved in 100 mL of 20:1 hexanes/EtOAc and the solution was filtered through a pad of silica gel. The filtrate was concentrated to give 11 g of the tite compound as a yellow oil.

$^1$H NMR (acetone-$d_6$, 400 MHz) 1.15 (6H, s), 2.60 (2H, d), 7.25–7.40 (5H, m), 7.95 (1H, t).
Step 4

5,5-Dimethyl-1-(4-(methylthio)phenyl)-2-phenylcyclopent-2-enol

To a −78° C. solution of p-bromothioanisole (5 g) in 100 mL of THF was added a solution n-BuLi (10 mL, 2.5 M in hexane). After stirring for 45 min. at −78° C., a solution of the product of Step 3 (2.4 g) in 10 mL of THF was added dropwise. The reaction mixture was stirred for 10 min. and then quenched with 100 mL of saturated solution of $NH_4Cl$. The product was extracted with 300 mL of 2:1 hexanes/EtOAc. The extract was dried over $Na_2SO_4$ and concentrated. Th e residue was purified by chromatography eluting with 10:1 hexane/EtOAc to give 3.5 g of the title compound.

$^1$H NMR (acetone-$d_6$, 400 MHz) 0.60 (3H, s), 1.25 (3H, s), 2.26 (1H, dd), 2.42 (1H, dd), 2.48 (3H, s), 4.12 (1H, s), 6.43 (1H, t), 7.10–7.40 (9H, m).
Step 5

5,5 Dimethyl-1-(4-(methylsulfonyl)phenyl)-2-phenylcyclopent-2-enol

To a solution of the product of Step 4 (1.92 g) in 130 mL of 10:1 $CH_2Cl_2$/MeOH cooled at 0° C. was added 5,5 g of MMPP. The reaction was stirred for 0.5 h at room temperature, diluted with 100 mL of 5:1 hexanes/EtOAc and then filtered through a pad of silica gel. The filtrate was concentrated and the residue was purified by chromatography eluting with 2:1 hexanes/EtOAc to give 1.8 g of the title compound.

$^1$H NMR (acetone-$d_6$, 400 MHz,) δ0.58 (3H, s), 1.27 (3H, s), 2.32 (1H, dd), 2.52 (1H, dd), 3.09 (3H, s), 4.46 (1H, s), 6.53 (1H, t), 7.12–7.20 (5H, m), 7.37 (2H, d), 7.85 (2H, d).
Step 6

4,4-Dimethyl-3-(4-(methylsulfonyl)pheny)-2-phenyl-2-cyclopenten-1-one

To a suspension of PCC (4 g) and 10 g of 4 Å molecular seives in 100 mL of $CH_2Cl_2$ was added a solution of the product of Step 5 (1.2 g) in 10 mL $CH_2Cl_2$. The reaction mixture was stirred for 12 hand then diluted with 200 mL of 1:1 hexanes/EtOAc, and filtered through a pad of silica gel.

The filtrate was concentrated and the residue was purified by chromatography eluting with 3:2 hexanes/EtOAc to give 200 mg of the title compound as a white solid.

$^1$H NMR (acetone-d$_6$, 400 MHz) δ1.36 (6H s), 2.62 (2H, s), 3.14 (3H, s), 7.10–7.20 (5H, m), 7.53 (2H, d), 7.96 (2H, d).

EXAMPLE 13

7-(4-(Methylsulfonyl)phenyl)-6-phenyl-4-oxa-spiro [2.4]-hept-6-en-5-one

Step 1

3-(Phenyl)-4-(4-(methylsulfonyl)phenyl)-2-(5H)-furanone

To a solution of phenylacetic acid (27.4 g, 201 mmol) and α-bromo-4-(methylsulfonyl)acetophenone (60 g, 216 mmol) in acetonitrile (630 mL) at 25° C. was added slowly triethylamine (30.8 mL). The mixture was stirred for 20 min at r.t. then cooled in an ice bath. DBU (60.1 mL) was slowly added. After 20 min, the mixture was quenched by the addition of 1N HCl followed by 2.4 L of ice water. The precipitate was filtered and rinsed with water to give 64 g of crude product. This solid was dissolved in 750 mL of dichloromethane, dried over MgSO$_4$ and filtered. Purification by flash chromatography eluting with 10% EtOAc/CH$_2$Cl$_2$, followed by an ethyl acetate swish provided 36.6 g (58%) of the title compound.

Analysis calculated for C$_{17}$H$_{14}$O$_4$S C, 64.95; H, 4,49; S, 10.20.

Found: C, 64.63; H, 4.65; S, 10.44.

Step 2

5-Hydroxymethyl-4-(4-(methylsulfonyl)phenyl)-3-phenyl-2-(5H)-furanone

A mixture of 3-phenyl-4-(4-(methylsulfonyl)phenyl)-2-(5H)-furanone from Step 1 (0.31 g, 1.0 mmol), 37% aqueous formaldehyde solution (0.1 mL), THF (20 mL) and water (5 mL) was treated with K$_2$CO$_3$ (20 mg, 0.15 mmol). After stirring for 1 h at room temperature, the reaction mixture was quenched with 15 mL of saturated aqueous NH$_4$Cl and extracted with 50 mL of EtOAc. The extract was dried over MgSO$_4$ and concentrated. The residue was purified by flash chromatography eluting with 3:1 EtOAc/hexanes to give 50 mg of the title compound along with 120 mg of 5,5-bis(hydroxymethyl)-3-phenyl-4-(4-(methylsulfonyl)phenyl)-2-(5H)-furanone.

$^1$H NMR (acetone-d$_6$, 400 MHz) δ3.15 (3H, s), 3.60 (1H, m), 4.03 (1H, m), 4.30 (1H, t), 5.72 (1H, t), 7.36 (5H, m), 7.66 (2H, d), 7.98 (2H, d).

Step 3

5-Methylene-4-(4-(methylsulfonyl)phenyl)-3-phenyl-2-(5H)-furanone

To a solution of the product of Step 2 (18 mg) and Et$_3$N (0.15 mL) in 10 mL of CH$_2$Cl$_2$ was added dropwise methanesulfonyl chloride at 0° C. After stirring for 10 min at 0° C., the reaction mixture was treated with 5 mL of saturated NaHCO$_3$ and extracted with 30 mL of 1:1 EtOAc/hexane. The extract was dried over MgSO$_4$ and concentrated to give 15 mg of the title compound as a white solid.

$^1$H NMR (acetone-d$_6$, 400 MHz) δ3.16 (3H, s), 4.92 (1H, d), 5.40 (1H, d), 7.30–7.42 (5H, m), 7.68 (2H, d), 8.06 (2H, d).

Step 4

7-(4-(methylsulfonyl)(phenyl)-6-phenyl-4-oxa-spiro [2.4]-hept-6-en-5one

A solution of the compound from Step 3 (450 mg) and Pd(OAc)$_2$ (150 mg) in 200 ml of Et$_2$O was cooled to 0° C. and treated with excess CH$_2$N$_2$ (in ether) until no starting material was observed by TLC. The reaction mixture was then filtered through a pad of silica gel and concentrated. The residue was purified by flash chromatography eluting with 2:1 hexanes/EtOAc to give 180 mg of the title compound as a yellow solid.

$^1$H NMR (acetone-$_6$, 400 MHz) δ1.32 (2H, m), 1.70 (2H, m), 3.16 (3H, s), 7.24–7.32 (3H, m), 7.36–7.44 (2H, m), 7.62 (2H, d), 8.05 (2H, d).

EXAMPLE 14

5,5-Bisfluoromethyl-3-phenyl-4-(4-(methylsulfonyl) phenyl)-2-(5H)-furanone

Step 1

5,5-Bis(hydroxymethyl)-3-phenyl-4-(4-(methylsulfonyl)phenyl)-2-(5H)-furanone

The title compound was obtained by the procedure described in Step 2 of Example 13.

$^1$H NMR (acetone-d$_6$, 400 MHz) δ3.16 (3H, s), 3.79 (2H, dd), 3.94 (2H, dd), 4.56 (2H, t), 7.20–7.35 (5H, m), 7.68 (2H, d), 8.04 (2H, d).

Step 2

5,5-Bisfluoromethyl-3-phenyl-4-(4-(methylsulfonyl) phenyl)2-(5H)-furanone

A solution of 5,5-bis(hydroxymethyl)-3-phenyl-4-(4-(methylsulfonyl)phenyl)-2-(5H)-furanone from Step 1 (0.55 g, 1.45 mmol) in 8 mL of CH$_2$Cl$_2$ was cooled to −78° C. and treated with Et$_2$NSF$_3$ (4 mL, 30 mmol). The mixture was then refluxed for 15 h and quenched by carefully pouring into 100 mL of saturated aqueous solution of NaHCO$_3$. The product was extracted with 150 mL of EtOAc. The extract was dried over MgSO$_4$ and concentrated. The residue was purified by flash chromatography eluting with 2:1 EtOAc/hexanes to give 0.4 g of the title product as a white solid.

$^1$H NMR (acetone-d$_6$, 400 MHz) δ3.14 (3H, s), 4.95 (4H, d), 7.25–7.40 (5H, m), 7.60 (2H, d), 8.06 (2H, d).

EXAMPLE 15

3-(3-Allyloxy-phenyl)-5,5-dimethyl-4-(4-methylsulfonyl-phenyl)-5H-furan-2-one

M.p. 128–129° C. $^1$H NMR (acetone-d$_6$, 300 MHz) δ8.05 (2H, m), 7.67 (2H, m), 7.31 (2H, m), 6.83 (2H, m), 6.04 (1H, m), 5.38 (1H, m), 5.22 (1H, m), 4.54 (2H, m), 3.18 (3H, s), 1.60 (6H, s).

EXAMPLE 16

3-(3,5-Difluoro-phenyl)-4-(4-methylsufonyl-phenyl)-1-oxa-spiro[4,4]non-3-en-2-one M.p. 186° C. Anal. calcd. for C$_{19}$H$_{16}$F$_2$O$_4$S: C, 60.31; H, 4.26; S, 8.47. Found: C, 60.34; H, 4.38; S, 8.66.

EXAMPLE 17

3-Chroman-7-yl-55,-dimethyl-4-(4-methylsulfonyl-phenyl)-5H-furan-2-one $^1$H NMR (acetone-d$_6$, 300 MHz) δ8.05 (2H, m), 7.64 (2H, m), 7.13 (1H, m), 6.97 (1H, m), 6.55 (1H, m), 4.11 (m, 2H), 3.18 (3H, s), 2.63 (2H, m), 1.90 (2H, m), 1.60 (6H, s).

EXAMPLE 18

4-(4-Methylsulfonyl-phenyl)-3-phenyl-5,5-bis-trifluoromethyl-5H-furanone

M.p. 138° C. Anal. calcd. for $C_{19}H_{12}F_6O_4S$: C, 50.67; H, 2.69; S, 7.12. Found: C, 50.90; H, 2.82; S, 7.14.

EXAMPLE 19

8-(4-Methylsulfonyl-phenyl)-7-phenyl-5-oxa-spiro[3.4]oct-7-en-6-one

Step 1

8-Hydroxy-7-phenyl-5-oxa-spiro[3.4]oct-7-en-6-one

To a solution of 1-hydroxy-cyclobutanecarboxylic acid (W. R. Jones et al. Organometallics 6, 2579 (1987) (3.8 g, 32.7 mmol) in $Et_2O$ (50 ml) at 0° C. was added an etheral solution of $CH_2N_2$ until the yellow color persisted. The solvent was evaporated to give 3.5 g of the corresponding methyl ester. The crude ester was dissolved in $CH_2Cl_2$ (66 ml) and cooled to 0° C. Pyridine (4.22 g, 53.3 mmol, 4.30 ml) was added, followed by dropwise addition of phenylacetyl chloride (6.18 g, 40 mmol, 5.3 ml) over a 0.5 h period. The mixture was stirred at 0° C. for 3 h and then poured into 5% aq. HCl (200 ml). The layers were separated and the aq. layer was extracted with $CH_2Cl_2$ (3×50 ml). The combined org. layers were washed with dil. aq. $NaHCO_3$ and brine (100 ml each) and dried over $MgSO_4$. Evaporation of the solvent and purification of the crude product by chromatography with 20% EtOAc in hexane gave the ester as an oil in quantitative yield.

A portion of the ester (2.18 g, 8.78 mmol) was dissolved in $CH_2Cl_2$ (44 ml) and cooled to 0° C. DBU (1.47 g, 9.66 mmol, 1.44 ml) was added and the mixture was allowed to stir at room temperature for 48 h. The dark solution was poured into 10% aq. HCl (100 ml) and the layers were separated. The aq. layer was extracted with $CH_2Cl_2$ (3×25 ml) and the combined org. layers were dried over $MgSO_4$. Evaporation of the solvent and purification by chromatography (10% EtOAc in toluene, 2.5% acetic acid) gave 460 mg of the title compound, mp 188–189° C.

Step 2

Trifluoro-methanesulfonic acid 6-oxo-7-phenyl-5-oxa-spiro[3.4]oct-7-en-8-yl ester To a solution of the lactone (460 mg, 2.12 mmol) in $CH_2Cl_2$ (15 ml) at 0° C. was added $NEt_3$ (258 mg, 2.55 mmol, 356 µl) followed by $Tf_2O$ (720 mg, 2.55 mmol, 429 µl). The solution was stirred for 1 h at 0° C. and then poured into water. The layers were separated and the aq. layer was extracted with $CH_2Cl_2$ (3×20 ml). The combined org. layers were dried over $MgSO_4$ and the solvent was evaporated to give 550 mg of the product as an oil.

Step 3

4-(Methylthio)benzeneboronic acid n-BuLi in hexane (2.5M, 625 mmol, 250 ml) is added slowly to a mechanically stirred solution of 4-bromothioanisole (100 g, 492 mmol) in THF (1 ) below −55° C. (internal temp.). After aging at −72° C. for 1 h trimethylborate (73 ml, 1.3 eq.) is added at such a rate to keep the internal temperature below −55° C. After 0.25 h at −78° C. the solution was allowed to warm to 0° C. for 10 min. 2N HCL (500 ml) is added and the solvent is evaporated. Water (500 ml) is added and the product is extracted with EtOAc (1.5 ). The organic layer is dried over $Na_2SO_4$, concentrated and the solid is stirred in hexane (500 ml) for 2 h. Filtartion gave 61.9 g (75%) of the desired product. $^1$H NMR (acetone-$d_6$, 400 MHz) δ7.80 (d, 2H), 7.22 (d, 2H), 7.15 (s, 2H), 2.50 (s, 3H).

Step 4

8-(4-Methylsulfanyl-phenyl)-7-phenyl-5-oxa-spiro[3.4]oct-7-en-6-one

To a solution of the triflate (550 mg, 1.58 mmol) from step 2 in THF (10 ml) and boronic acid from step 3 (318 mg, 1.90 mmol) was added an aq. solution of $Na_2CO_3$ (2.0M, 3.16 mmol, 1.60 ml) and $Pd(PPh_3)_4$ (91 mg, 0.079 mmol). The mixture was heated for 2 h at 70° C., cooled and poured into sat. aq. $NH_4Cl$. The aq. layer was extracted with $Et_2O$ and the combined org. layers were dried over $MgSO_4$. Purification via flash chromatography (20% EtOAc in hexane) gave 460 mg of the title compound as a foam.

Step 5

8-(4-Methylsulfonyl-phenyl)-7-phenyl-5-oxa-spiro[3.4]oct-7-en-6-one

To the thioether from step 3 (460 mg, 1.43 mmol) in $CH_2Cl_2$ (17 ml) and MeOH (4.3 ml) at 0° C. was added MMPP (970 mg, 1.57 mmol) in two portions. The ice bath was removed and the mixture was stirred at room temperature for 2 h. The suspension was filtered and the filtrate was washed with sat. aq. $NaHCO_3$ and water. After drying over $MgSO_4$ and evaporation of the solvent a yellow foam was obtained. Stirring of this foam with 10 ml $Et_2O$ for 1 h and filtration gave 417 mg of the title compound as a colorless solid, m.p. 159–160° C.

EXAMPLE 20

6-(3-Fluorophenyl)-7-(4-(methylsulfonyl)phenyl)-4-oxa-spiro[2.4]hept-6-en-5-one

Following method N, example 19 and substituting 1-hydroxy-cyclopropanecarboxylic acid for 1-hydroxy-cyclobutanecarboxylic acid, the tide compound was obtained as a colorless solid. M.p. 130–131° C.

EXAMPLE 21

7-(4-Methylsulfonylphenyl)-6-naphthalen-2-yl-4-oxa-spiro[2.4]hept-6-en-5-one

Following method N, example 19 and substituting 1-hydroxy-cyclopropanecarboxylic acid for 1-hydroxy-cyclobutanecarboxylic acid, the title compound was obtained as a colorless solid. $^1$H NMR (acetone-$d_6$, 400 MHz) δ1.36–1.39 (2H, m), 1.73–1.76 (2H, m), 3.16 (3H, s), 7.35–7.38 (1H, m), 7.48–7.52 (2H, m), 7.65–7.85 (5H, m), 8.03–8.08 (3H, m).

EXAMPLE 22

4-(6-Naphthalen-2-yl-5-oxo-4-oxa-spiro[2.4]hept-6-en-7-yl)-benzenesulfonamide

Following method N, example 19 and substituting 1-hydroxy-cyclopropanecarboxylic acid for 1-hydroxy-cyclobutanecarboxylic acid, the title compound was obtained as a colorless solid. $^1$H NMR (acetone-$d_6$, 300 MHz) δ1.32–1.48 (2H, m), 1.70–1.75 (2H, m), 6.70 (1H, bs), 7.34 (1H, dd), 7.46–7.60 (4H, m), 7.70–8.10 (6H, m).

EXAMPLE 23

7-(4-Fluorophenyl)-8-(4-methylsulfonylphenyl)-5-oxa-spiro[3.4]oct-7-en-6-one

Anal. calcd. for $C_{20}H_{17}FO_4S$: C, 64.50; H, 4.60. Found: C, 64,46; H, 4.62.

EXAMPLE 24

7-(3-Fluorophenyl)-8-(4-methylsulfonylphenyl)-5-oxa-spiro[3.4]oct-7-en-6-one

Anal. calcd. for $C_{20}H_{17}FO_4S$: C, 64.50; H, 4.60. Found: C, 64,44; H, 4.75.

EXAMPLE 25

7-(3,4-Difluorophenyl)-8-(4-methylsulfonylphenyl)-5-oxa-spiro[3.4]oct-7-en-6-one $^1$H NMR (acetone-$d_6$, 400 MHz) δ1.15–1.22 (1H, m), 1.82–1.90 (1H, m), 2.62–2.80 (4H, m), 3.20 (3H, s), 7.10–7.25 (2H, m), 7.32–7.40 (1H, m), 7.82–7.86 (2H, dd), 8.10–8.16 (2H,dd).

EXAMPLE 26

4-(6-Oxo-7-phenyl-5-oxa-spiro[3.4]oct-7-en-8-yl)-benzenesulfonamide

M.p. 162–163° C.

EXAMPLE 27

4-[7-(4-Fluorophenyl)-6oxo-5-oxa-spiro[3.4]oct-7-en-8-yl]-benzenesulfonamide

Anal. calcd. for $C_{19}H_{16}FNO_4S$: C, 61.12; H, 4.32; N, 3.75. Found: C, 61.18; H, 4.49; N, 3.77.

EXAMPLE 28

4-[7-(3-Fluorophenyl)-6oxo-5-oxa-spiro[3.4]oct-7-en-8-yl]-benzenesulfonamide

Anal. calcd. for $C_{19}H_{16}FNO_4S$: C, 61.12; H, 4.32; N, 3.75. Found: C, 61.00; H, 4.56; N, 3.76.

EXAMPLE 29

4-[7-(3,4-Difluorophenyl)-6-oxo-5-oxa-spiro[3.4]oct-7-en-8-yl]-benzenesulfonamide $^1$H NMR (acetone-$d_6$, 400 MHz) δ1.12–1.24 (1H, m), 1.80–1.92 (1H,m), 2.61–2.70 (4H, m), 6.73 (1H, bs), 7.12–7.26 (2H, m), 7.31–7.40 (1H, m), 7.73–7.75 (2H, dd), 8.03–8.06 (2H, dd).

EXAMPLE 30

3-(4-Fluorophenyl)-4-(4-(methylsulfonyl)phenyl)-1-oxa-spiro[4.4]non-3-en-2-one

M.p. 166–167° C. Anal. calcd. for $C_{21}H_{19}FO_4S$: C, 65.27; H, 4.96; S, 8.30. Found: C, 65.11; H, 5.10; S, 8.07.

EXAMPLE 31

3-(3-Fluorophenyl)-4-(4-(methylsulfonyl)phenyl)-1-oxa-spiro[4.4]non-3-en-2-one

M.p. 158–159° C. Anal. calcd. for $C_{21}H_{19}FO_4S$: C, 65.27; H, 4.96; S, 8.30. Found: C, 65.13; H, 5.12; S, 8.56.

EXAMPLE 32

3-(3,4-Difluorophenyl)-4-(4-(methylsulfonyl)phenyl)-1-oxa-spiro[4.4]non-3-en-2-one M.p. 149.5–150.5° C. Anal. calcd. for $C_{21}H_{18}F_2O_4S$: C, 62.37; H, 4,49; S, 7.93. Found: C, 62.43; H, 4.64; S, 8.42.

EXAMPLE 33

3-(3-Chloro-4-fluorophenyl)-4-(4-(methylsulfonyl)phenyl)-1-oxa-spiro[4.4]non-3-en-2-one $^1$H NMR (acetone-$d_6$, 300 MHz) δ1.60–2.20 (8H, m), 3.20 (3H, s), 7.20 (1H, t), 7.30 (1H, m), 7.55 (1H, dd), 7.70 (2H, d), 8.10 (2H, d). Anal. calcd. for $C_{21}H_{18}ClFO_4S$: C, 60.00; H, 4.28. Found: C, 60.02; H, 4.42.

EXAMPLE 34

4-(2-Oxo-3-phenyl-1-oxa-spiro[4.4]non-3-en-4-yl)-benzenesulfonamide

M.p. 173° C. Anal. calcd. for $C_{20}H_{19}NO_4S$ 1/2 EtOAc: C, 63.91; H, 5.61; N, 3,39; S, 7.75. Found: C, 64.14; H, 5.74; N, 3,36; S, 7.70.

EXAMPLE 35

4-[3-(4-Fluorophenyl)-2-oxo-1-oxa-spiro[4.4]non-3-en-4-yl)]-benzenesulfonamide

M.p. 169° C. Anal. calcd. for $C_{20}H_{18}FNO_4S$ 1/2 EtOAc: C, 61.24; H, 5.14; N, 3.25; S, 7.43. Found: C, 61.19; H, 5.29; N, 3.21; S, 7.40.

EXAMPLE 36

4-[3-(3-Fluorophenyl)-2-oxo-1-oxa-spiro[4.4]non-3-en-4-yl)]-benzenesulfonamide

M.p. 142–144° C. Anal. calcd. for $C_{20}H_{18}FO_4S$: C, 62.00; H, 4.68; N, 3.62. Found: C, 61.83; H, 4.90; N, 3.53.

EXAMPLE 37

4-[3-(3,4-Difluorophenyl)-2-oxo-1-oxa-spiro[4.4]non-3-en-4-yl)]-benzenesulfonamide M.p.>92° C. Anal. calcd. for $C_{20}H_{17}F_2O_4S$: C, 59.25; H, 4.23; N, 3.45. Found: C, 59.22; H, 4.34; N, 3.37.

EXAMPLE 38

4-[3-(3-Chloro-4-fluorophenyl)-2-oxo-1-oxa-spiro[4.4non-3en-4yl]-benzenesulfonamide $^1$H NMR (acetone-$d_6$, 300 MHz) δ1.70–2.20 (8H, m), 6.60 (2H, bs), 7.20 (1H, t), 7.25 (1H,m), 7.55 (3H, m), 8.00 (2H, d). M/z 422 (M+H)$^+$.

EXAMPLE 39

4-(4-(Methylsulfonyl)phenyl)-1-oxa-spiro[4.5]dec-3-en-2-one

M.p. 222–223° C.

EXAMPLE 40

4-(2-Oxo-3-phenyl-1-oxa-spiro[4.5]dec-3-en-4-yl)-benzenesulfonamide

M.p. 213° C. Anal. calcd for $C_{21}H_{21}NO_4S$: C, 65.78; H, 5,52; N, 3.65; S, 8.36. Found: C, 65.62; H, 5,56; N, 3.47; S, 8.44.

EXAMPLE 41

4-[3-(4-Fluorophenyl)-2-oxo-1-oxa-spiro[4.5]dec-3-en-4-yl)-benzenesulfonamide

M.p. 202–203° C. Anal. calcd. for $C_{21}H_{20}FNO_4S$: C, 62.83; H, 5.02; N, 3.49; S, 7.99. Found: C, 62.66; H, 5.04; N, 3.48; S, 8.08.

What is claimed is:

1. A compound of formula I

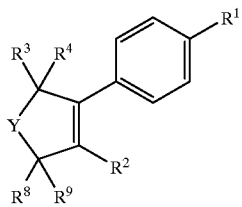

or a pharmaceutically acceptable salt thereof wherein:

Y is oxygen, $R^1$ is selected from the group consisting of
(a) $S(O)_2CH_3$,
(b) $S(O)_2NH_2$,
(c) $S(O)_2NHC(O)CF_3$,
(d) $S(O)(NH)NH_2$,
(e) $S(O)(NH)NHC(O)CF_3$,
(f) $P(O)(CH_3)NH_2$,
(g) $P(O)(CH_3)_2$, $R^2$ is selected from the group consisting of
(a) $C_{1-6}$alkyl,
(b) $C_{3-7}$cycloalkyl,
(c) mono-, di- or tri-substituted phenyl or naphthyl wherein the substituent is selected from the group consisting of
  (1) hydrogen,
  (2) halo,
  (3) $C_{1-6}$alkoxy,
  (4) $C_{1-6}$alkylthio,
  (5) CN,
  (6) $CF_3$,
  (7) $C_{1-6}$alkyl,
  (8) $N_3$,
  (9) —$CO_2H$,
  (10) —$CO_2$—$C_{1-4}$alkyl,
  (11) —$C(R^5)(R^6)$—OH,
  (12) —$C(R^5)(R^6)$—O—$C_{1-4}$alkyl, and
  (13) —$C_{1-6}$alkyl—$CO_2$—$R^5$;
  (14) benzyloxy,
  (15) —O—($C_{1-6}$alkyl)—$CO_2R^5$,
  (16) —O—($C_{1-6}$alkyl)—$NR^5R^6$;
(d) mono-, di- or tri-substituted heteroaryl wherein the heteroaryl is a monocyclic aromatic ring of 5 atoms, said ring having one hetero atom which is S, O, or N, and 0–3 additional N atoms; or
the heteroaryl is a monocyclic ring of 6 atoms, said ring having one hetero atom which is N, and 0–4 additional N atoms, said substituents are selected from the group consisting of
  (1) hydrogen,
  (2) halo,
  (3) $C_{1-6}$alkyl,
  (4) $C_{1-6}$alkoxy,
  (5) $C_{1-6}$alkylthio,
  (6) CN,
  (7) $CF_3$,
  (8) $N_3$,
  (9) —$C(R^5)(R^6)$—OH, and
  (10) —$C(R^5)(R^6)$—O—$C_{1-4}$alkyl;
(e) a mono- or di-substituted benzoheterocycle in which the heterocycle is a 5, 6, or 7-membered ring which contains 0–2 heteroatoms chosen independently from O, S, or N and which contains or does not contain a carbonyl group or a sulfonyl group; the said substituents are selected from the group consisting of
  (1) hydrogen,
  (2) halo,
  (3) $C_{1-6}$alkyl,
  (4) $C_{1-6}$alkoxy,
  (5) $C_{1-6}$alkylthio,
  (6) CN,
  (7) $CF_3$,
  (8) $N_3$,
  (9) —$C(R^5)(R^6)$—OH, and
  (10) —$C(R^5)(R^6)$—O—$C_{1-4}$alkyl;
(f) a heterocycloalkyl group of 5–7 members which contains 1 or 2 heteroatoms chosen from O, S, or N and contains or does not contain a carbonyl group or a sulfonyl group;
(g) a mono- or di-substituted benzocarbocycle in which the carbocycle is a 5, 6, or 7-membered ring which contains or does not contain a carbonyl group, the said substituents are selected from the group consisting of
  (1) hydrogen,
  (2) halo,
  (3) $C_{1-6}$alkyl,
  (4) $C_{1-6}$alkoxy,
  (5) $C_{1-6}$alkylthio,
  (6) CN,
  (7) $CF_3$,
  (8) $N_3$,
  (9) —$C(R^5)(R^6)$—OH, and
  (10) —$C(R^5)(R^6)$—O—$C_{1-4}$alkyl;

$R^3$ is a mono- or di-substituted phenyl, a mono- or di-substituted benzyl, a mono- or di-substituted heteroaryl, a mono- or di-substituted heteroarylmethyl wherein the substituents are selected from
  (1) hydrogen,
  (2) halo,
  (3) $C_{1-6}$alkyl,
  (4) $C_{1-6}$alkoxy,
  (5) $C_{1-6}$alkylthio,
  (6) CN,
  (7) $CF_3$,
  (8) $N_3$,
  (9) —$C(R^5)(R^6)$—OH, and
  (10) —$C(R^5)(R^6)$—O—$C_{1-4}$alkyl;

$CH_2OR^7$, CN, $CH_2CN$, $C_{1-6}$fluoroalkyl, F or $CONR^7_2$;

$R^4$ is
(a) a mono- or di-substituted phenyl, a mono- or di-substituted benzyl, a mono- or di-substituted heteroaryl or a mono- or di-substituted heteroarylmethyl as defined above, said substituents are selected from the group consisting of
  (1) hydrogen,
  (2) halo,
  (3) $C_{1-6}$alkyl,
  (4) $C_{1-6}$alkoxy,
  (5) $C_{1-6}$alkylthio,
  (6) CN,
  (7) $CF_3$,
  (8) $N_3$,
  (9) —$C(R^5)(R^6)$—OH, and
  (10) —$C(R^5)(R^6)$—O—$C_{1-4}$alkyl, or
(b) $C_{1-7}$alkyl, $CH_2OR^7$, CN, $CH_2CN$, $C_{1-6}$fluoroalkyl, F or $CONR^7_2$ or $R^3$ and $R^4$ together with the carbon to which they are attached form a saturated monocyclic ring of 3, 4, 5, 6 or 7 atoms, containing 0–2 heteroatoms chosen independently from O, S and N, and hexa-substituted by $R^{12}$ and containing or not containing a carbonyl or sulfonyl group;

each $R^{12}$ is independently selected from the group consisting of
- (a) hydrogen,
- (b) $C_{1-6}$alkyl,
- (c) phenyl or monosubstituted phenyl wherein the substituent is selected from the group consisting of: halo, $C_{1-6}$alkyl, $C_{1-6}$alkoxy, $C_{1-6}$alkylthio, CN, and $CF_3$,
- (d) benzyl or monosubstituted benzyl wherein the substituent is selected from the group consisting of: halo, $C_{1-6}$alkyl, $C_{1-6}$alkoxy, $C_{1-6}$alkylthio, CN, and $CF_3$,
- (e) —$CO_2$-alkyl,
- (f) halo, $R^5$, $R^6$ and $R^7$ are each independently selected from the group consisting of
- (a) hydrogen, and
- (b) $C_{1-6}$alkyl, or $R^5$ and $R^6$ together with the carbon to which they are attached form a saturated monocyclic carbon ring of 3, 4, 5, 6 or 7 atoms;

$R^8$ and $R^9$ are independently selected from the group consisting of:
- (a) hydrogen,
- (b) $C_{1-7}$alkyl, or $R^8$ and $R^9$ together form a double bonded O or S;

$R^{10}$ and $R^{11}$ are independently
- (a) hydrogen,
- (b) a mono- or di-substituted phenyl, a mono- or di-substituted benzyl, a mono- or di-substituted heteroaryl, or a mono- or di-substituted heteroarylmethyl, said substituents are selected from the group consisting of
  - (1) hydrogen,
  - (2) halo,
  - (3) $C_{1-6}$alkyl,
  - (4) $C_{1-6}$alkoxy,
  - (5) $C_{1-6}$alkylthio,
  - (6) CN,
  - (7) $CF_3$,
  - (8) $N_3$,
  - (9) —$C(R^{13})(R^{14})$—OH, and
  - (10) —$C(R^{13})(R^{14})$—O—$C_{1-4}$alkyl, or
- (c) $C_{1-7}$alkyl, $CH_2OR^7$, CN, $CH_2CN$, $C_{1-6}$fluoroalkyl, F or $CONR^7_2$, or
- (d) $R^{10}$ and $R^{11}$ together form a double bonded O; or $R^{10}$ and $R^{11}$ together with the carbon to which they are attached form a saturated monocyclic carbon ring of 3, 4, 5, 6 or 7 atoms;

$R^{13}$ and $R^{14}$ are independently selected from the group consisting of:
- (a) hydrogen,
- (b) $C_{1-7}$alkyl, or $R^{13}$ and $R^{14}$ together form a double bonded O or S.

2. A compound according to claim 1 of formula Ia

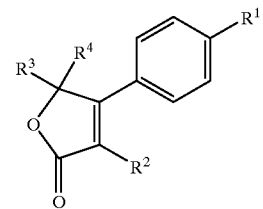

Ia wherein:

$R^1$ is selected from the group consisting of
- (a) $S(O)_2CH_3$,
- (b) $S(O)_2NH_2$,
- (c) $S(O)_2NHC(O)CF_3$,
- (d) $S(O)(NH)NH_2$,
- (e) $S(O)(NH)NHC(O)CF_3$,
- (f) $P(O)(CH_3)NH_2$,
- (g) $P(O)(CH3)2$ $R^2$ is selected from the group consisting of
- (a) $C_{1-6}$alkyl,
- (b) $C_3$, $C_4$, $C_5$ or $C_6$ cycloalkyl,
- (c) mono-, di- or tri-substituted phenyl or naphthyl wherein the substituent is selected from the group consisting of
  - (1) hydrogen,
  - (2) halo,
  - (3) $C_{1-6}$alkoxy,
  - (4) $C_{1-6}$alkylthio,
  - (5) CN,
  - (6) $CF_3$,
  - (7) $C_{1-6}$alkyl,
  - (8) $N_3$,
  - (9) —$CO_2H$,
  - (10) —$CO_2$—$C_{1-4}$alkyl,
  - (11) —$C(R^5)(R^6)$—OH,
  - (12) —$C(R^5)(R^6)$—O—$C_{1-4}$alkyl, and
  - (13) —$C_{1-6}$alkyl—$CO_2$—$R^5$;
  - (14) benzyloxy,
  - (15) —O—($C_{1-6}$alkyl)—$CO_2R^5$
  - (16) —O—($C_{1-6}$alkyl)—$NR^5R^6$
- (d) mono- or di-substituted heteroaryl selected from the group consisting of
  - (1) furanyl,
  - (2) diazinyl, triazinyl and tetrazinyl,
  - (3) imidazolyl,
  - (4) isooxazolyl,
  - (5) isothiazolyl,
  - (6) oxadiazolyl,
  - (7) oxazolyl,
  - (8) pyrazolyl,
  - (9) pyrrolyl,
  - (10) thiadiazolyl,
  - (11) thiazolyl,
  - (12) thienyl,
  - (13) triazolyl, and
  - (14) tetrazolyl, wherein said substituents are selected from the group consisting of
- (1) hydrogen,
- (2) fluoro, chloro, bromo and iodo,
- (3) $C_{1-6}$alkyl,
- (4) $C_{1-6}$alkoxy,
- (5) $C_{1-6}$alkylthio,
- (6) CN, (7) $CF_3$,
(8) $N_3$,
(9) —$C(R^5)(R^6)$—OH, and
(10) —$C(R^5)(R^6)$—O—$C_{1-4}$alkyl;
(e) a mono- or di-substituted benzoheterocycle, benzocarbocycle or heterocycloalkyl selected from the group consisting of
(1) 2-indolyl,
(2) 3-indolyl,
(3) 1-methyl-5-indolyl
(4) 2-benzofuranyl,
(5) 3-benzofuranyl,
(6) 5-benzofuranyl,
(7) 6-benzofuranyl,
(8) 2-benzothienyl,
(9) 3-benzothienyl,
(10) 5-benzothienyl,
(11) 6-benzothienyl,
(12)
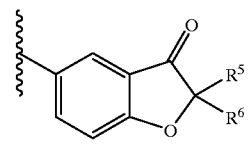
(13)
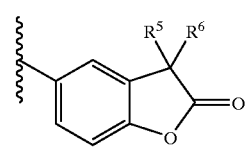
(14)
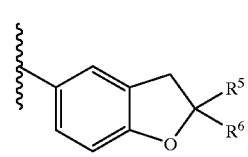
(15)
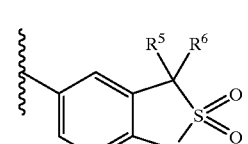
(16)
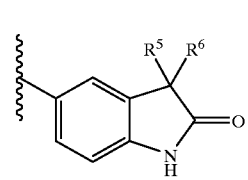
(17)
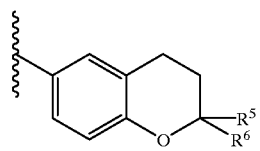
(18)
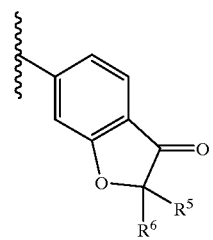
(19)
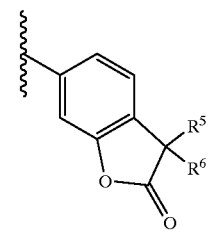
(20)
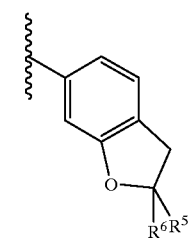
(21)
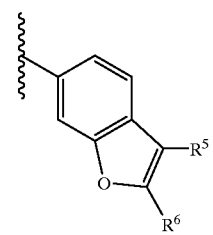
(22)
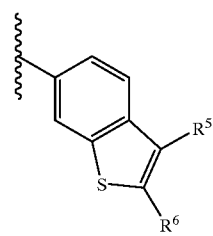
(23)
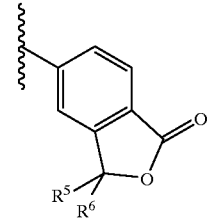

(24) 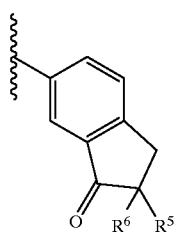

(25) 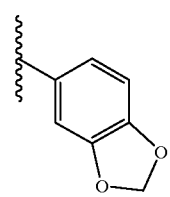

(26) 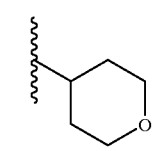

(27) 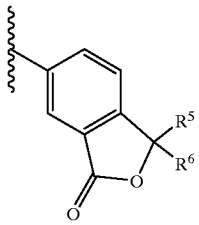

(28) 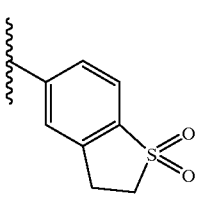

(29) 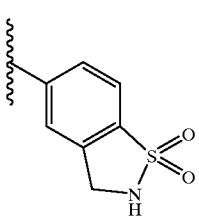

(30) 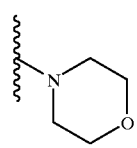

(31) 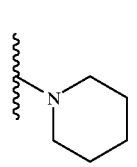

(32) 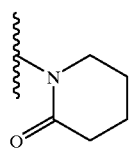

(33) 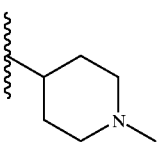

wherein said substituents are selected from the group consisting of
(1) hydrogen,
(2) halo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH, and
(10) —$C(R^5)(R^6)$—O—$C_{1-4}$alkyl;

$R^3$ is $CH_2OR^7$, CN, $CH_2CN$, or $C_{1-6}$fluoroalkyl;

$R^4$ is
(a) a mono- or di-substituted phenyl or a mono- or di-substituted heteroaryl, said substituents are selected from the group consisting of
(1) hydrogen,
(2) halo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH, and
(10) —$C(R^5)(R^6)$—O—$C_{1-4}$alkyl, or
(b) $C_{1-6}$alkyl, $CH_2OR^7$, CN, $CH_2CN$, or $C_{1-6}$fluoroalkyl; or $R^3$ and $R^4$ together with the carbon to which they are attached form a saturated monocyclic ring of 3, 4, 5, 6 or 7 atoms, containing 0–2 heteroatoms chosen independently from O, S and N, and hexa-substituted by $R^{12}$, each $R^{12}$ is independently selected from the group consisting of
(a) hydrogen,
(b) $C_{1-6}$alkyl,
(c) phenyl or monosubstituted phenyl wherein the substituent is selected from the group consisting of: halo, $C_{1-6}$alkyl, $C_{1-6}$alkoxy, $C_{1-6}$alkylthio, CN, and $CF_3$,
(d) benzyl or monosubstituted benzyl wherein the substituent is selected from the group consisting of: halo, $C_{1-6}$alkyl, $C_{1-6}$alkoxy, $C_{1-6}$alkylthio, CN, and $CF_3$,
(e) —$CO_2$-alkyl,
(f) halo;

$R^5$, $R^6$ and $R^7$ are each independently selected from the group consisting of
(a) hydrogen, and (b) $C_{1-6}$alkyl, or $R^5$ and $R^6$ together with the carbon to which they are attached form a saturated monocyclic carbon ring of 3, 4, 5, 6 or 7 atoms.

3. A compound according to claim 2 of formula Ia

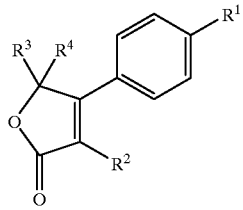

Ia wherein:

$R^1$ is selected from the group consisting of
(a) $S(O)_2CH_3$,
(b) $S(O)_2NH_2$,
(c) $S(O)_2NHC(O)CF_3$,
(d) $S(O)(NH)NH_2$,
(e) $S(O)(NH)NHC(O)CF_3$,
(f) $P(O)(CH_3)NH_2$,
(g) $P(O)(CH3)2$ $R^2$ is selected from the group consisting of
(a) cyclohexyl, and
(b) mono-, di- or tri-substituted phenyl or naphthyl wherein the substituent is selected from the group consisting of
(1) hydrogen,
(2) halo,
(3) $C_{1-4}$alkoxy,
(4) $C_{1-4}$alkylthio,
(5) CN,
(6) $CF_3$,
(7) $C_{1-4}$alkyl,
(8) $N_3$,
(9) —$CO_2H$,
(10) —$CO_2$—$C_{1-4}$alkyl,
(11) —$C(R^5)(R^6)$—OH,
(12) —$C(R^5)(R^6)$—O—$C_{1-4}$alkyl, and
(13) —$C_{1-6}$alkyl—$CO_2$—$R^5$,
(14) benzyloxy,
(15) —O—($C_{1-4}$alkyl)—$CO_2R^5$,
(16) —O—($C_{1-4}$alkyl)—$NR^5R^6$;

$R^3$ is $CH_2OR^7$, CN, $CH_2CN$, or $C_{1-6}$fluoroalkyl;

$R^4$ is
(a) a mono- or di-substituted phenyl or a mono- or di-substituted heteroaryl, said substituents are selected from the group consisting of
(1) hydrogen,
(2) halo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH, and
(10) —$C(R^5)(R^6)$—O—$C_{1-4}$alkyl, or
(b) $C_{1-6}$alkyl, $CH_2OR^7$, CN, $CH_2CN$, or $C_{1-6}$fluoroalkyl; or $R^3$ and $R^4$ together with the carbon to which they are attached form a saturated monocyclic ring of 3, 4, 5, 6 or 7 atoms, containing 0–2 heteroatoms chosen independently from O, S and N, and substituted by tetra-$R^{12}$, each $R^{12}$ is independently selected from the group consisting of
(a) hydrogen,
(b) $C_{1-6}$alkyl,
(c) phenyl or monosubstituted phenyl wherein the substituent is selected from the group consisting of: halo, $C_{1-6}$alkyl, $C_{1-6}$alkoxy, $C_{1-6}$alkylthio, CN, and $CF_3$,
(d) benzyl or monosubstituted benzyl wherein the substituent is selected from the group consisting of: halo, $C_{1-6}$alkyl, $C_{1-6}$alkoxy, $C_{1-6}$alkylthio, CN, and $CF_3$,
(e) —$CO_2$-alkyl,
(f) halo, $R^5$, $R^6$ and $R^7$ are each independently selected from the group consisting of
(a) hydrogen, and
(b) $C_{1-6}$alkyl, or $R^5$ and $R^6$ together with the carbon to which they are attached form a saturated monocyclic carbon ring of 3, 4, 5, 6 or 7 atoms.

4. A compound according to claim 3 of formula Ia

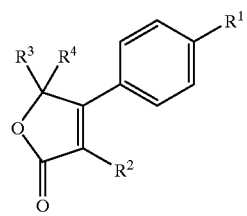

Ia wherein:

$R^1$ is selected from the group consisting of
(a) $S(O)_2CH_3$,
(b) $S(O)_2NH_2$,
(c) $S(O)(NH)NH_2$, $R^2$ is selected from the group consisting of
mono-, di- or tri-substituted phenyl or naphthyl wherein the substituent is selected from the group consisting of
(1) hydrogen,
(2) halo,
(3) $C_{1-4}$alkoxy,
(4) $C_{1-4}$alkylthio,
(5) CN,
(6) $CF_3$,
(7) $C_{1-4}$alkyl,
(8) $N_3$,
(9) —$CO_2H$,
(10) —$CO_2$—$C_{1-4}$alkyl,
(11) —$C(R^5)(R^6)$—OH,
(12) —$C(R^5)(R^6)$—O—$C_{1-4}$alkyl, and
(13) —$C_{1-4}$alkyl-$CO_2$—$R^5$;

$R^3$ is $CH_2OR^7$, CN, $CH_2CN$, or $C_{1-4}$fluoroalkyl;

$R^4$ is
(a) a mono- or di-substituted phenyl or a mono- or di-substituted heteroaryl, said substituents are selected from the group consisting of
(1) hydrogen,
(2) fluoro, chloro and bromo,
(3) $C_{1-4}$alkyl,
(4) $C_{1-4}$alkoxy,
(5) $C_{1-4}$alkylthio,
(6) CN, (7) $CF_3$, or (b) $C_{1-4}$alkyl, $CH_2OR^7$, CN, $CH_2CN$, or $C_{1-4}$fluoroalkyl; or $R^3$ and $R^4$ together with the carbon to which they are attached form a saturated monocyclic ring of 3, 4, 5, 6 or 7 atoms, containing 0–2 heteroatoms chosen independently from O, S and N, and substituted by tri-$R^{12}$, each $R^{12}$ is independently selected from the group consisting of (a) hydrogen,
(b) $C_{1-4}$alkyl,
(c) phenyl or monosubstituted phenyl wherein the substituent is selected from the group consisting of: halo, $C_{1-4}$alkyl, $C_{1-4}$alkoxy, $C_{1-6}$alkylthio, CN, and $CF_3$,
(d) benzyl or monosubstituted benzyl wherein the substituent is selected from the group consisting of: halo, $C_{1-4}$alkyl, $C_{1-4}$alkoxy, $C_{1-4}$alkylthio, CN, and $CF_3$,
(e) —$CO_2$—$C_{1-4}$alkyl,
(f) halo, $R^5$, $R^6$ and $R^7$ are each independently selected from the group consisting of (a) hydrogen, and
(b) $C_{1-4}$alkyl, or $R^5$ and $R^6$ together with the carbon to which they are attached form a saturated monocyclic carbon ring of 3, 4, 5, 6 or 7 atoms.

5. A compound according to claim 4 of formula Ia

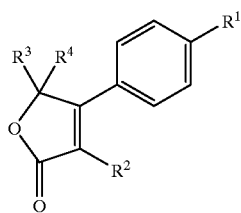

Ia wherein:

$R^1$ is selected from the group consisting of
(a) $S(O)_2CH_3$,
(b) $S(O)_2NH_2$, $R^2$ is selected from the group consisting of
mono-, di- or tri-substituted phenyl or naphthyl wherein the substituent is selected from the group consisting of
(1) hydrogen,
(2) halo,
(3) $C_{1-4}$alkoxy,
(4) $C_{1-4}$alkylthio,
(5) CN,
(6) $CF_3$,
(7) $C_{1-4}$alkyl,
(8) $N_3$, and
(9) —$C(R^5)(R^6)$—OH;

$R^3$ is $CH_2OR^7$, CN, $CH_2CN$, or $C_{1-3}$fluoroalkyl;
$R^4$ is
(a) a mono- or di-substituted phenyl or a mono- or di-substituted heteroaryl, said substituents are selected from the group consisting of
(1) hydrogen,
(2) halo,
(3) $C_{1-3}$alkyl,
(4) $C_{1-3}$alkoxy,
(5) $C_{1-4}$alkylthio,
(6) CN,
(7) $CF_3$, or (b) $C_{1-3}$alkyl, $CH_2OR^7$, CN, $CH_2CN$, or $C_{1-3}$fluoroalkyl;

$R^5$, $R^6$ and $R^7$ are each independently selected from the group consisting of
(a) hydrogen, and
(b) $C_{1-3}$alkyl.

6. A compound according to claim 5 of formula Ia

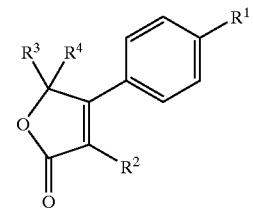

wherein:

$R^1$ is selected from the group consisting of
(a) $S(O)_2CH_3$,
(b) $S(O)_2NH_2$, $R^2$ is selected from the group consisting of
mono-, di- or tri-substituted phenyl or naphthyl wherein the substituent is selected from the group consisting of
(1) hydrogen,
(2) halo, selected from the group consisting of fluoro, chloro and bromo,
(3) $C_{1-3}$alkoxy,
(4) $C_{1-3}$alkylthio,
(5) CN, and
(6) $C_{1-3}$alkyl.

$R^3$ is $CH_2OR^7$, CN, $CH_2CN$, or $C_{1-3}$fluoroalkyl;
$R^4$ is
(a) a mono- or di-substituted phenyl or a mono- or di-substituted heteroaryl, said substituents are selected from the group consisting of
(1) hydrogen,
(2) halo,
(3) $C_{1-3}$alkyl,
(4) $C_{1-3}$alkoxy,
(5) $C_{1-4}$alkylthio,
(6) $CF_3$, or (b) $C_{1-3}$alkyl, $CH_2OR^7$, CN, $CH_2CN$, or $C_{1-3}$fluoroalkyl;

$R^5$, $R^6$ and $R^7$ are each independently selected from the group consisting of
(a) hydrogen, and
(b) $C_{1-3}$alkyl.

7. A compound according to claim 6 of formula Ia

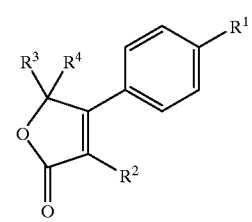

Ia wherein:

$R^1$ is selected from the group consisting of

S(O)$_2$CH$_3$, $R^2$ is selected from the group consisting of
mono-, di- or tri-substituted phenyl or naphthyl wherein the substituent is selected from the group consisting of
(1) hydrogen,
(2) halo, selected from the group consisting of fluoro, chloro and bromo,
(3) methoxy,
(4) methylthio,
(5) CN, and
(6) methyl and ethyl, $R^3$ is CH$_2$OR$^7$, CN, CH$_2$CN, or trifluoromethyl;

$R^4$ is
(a) a mono- or di-substituted phenyl or a mono- or di-substituted heteroaryl, said substituents are selected from the group consisting of
(1) hydrogen,
(2) fluoro, chloro and bromo,
(3) methyl and ethyl,
(4) methoxy,
(5) methylthio,
(6) CF$_3$, or
(b) C$_{1-3}$alkyl, CH$_2$OR$^7$, CN, CH$_2$CN, or trifluoromethyl;

$R^5$, $R^6$ and $R^7$ are each independently selected from the group consisting of
(a) hydrogen, and
(b) methyl.

8. A compound according to claim 2 wherein $R^2$ is selected from the group consisting of
(a) mono- or di-substituted heteroaryl selected from the group consisting of
(1) furanyl,
(2) diazinyl, triazinyl and tetrazinyl,
(3) imidazolyl,
(4) isooxazolyl,
(5) isothiazolyl,
(6) oxadiazolyl,
(7) oxazolyl,
(8) pyrazolyl,
(9) pyrrolyl,
(10) thiadiazolyl,
(11) thiazolyl,
(12) thienyl,
(13) triazolyl, and
(14) tetrazolyl,
wherein said substituents are selected from the group consisting of
(1) hydrogen,
(2) fluoro, chloro, bromo and iodo,
(3) C$_{1-6}$alkyl,
(4) C$_{1-6}$alkoxy,
(5) C$_{1-6}$alkylthio,
(6) CN,
(7) CF$_3$,
(8) N$_3$,
(9) —C(R$^5$)(R$^6$)—OH, and
(10) —C(R$^5$)(R$^6$)—O—C$_{1-4}$alkyl;
(b) a mono- or di-substituted benzoheterocycle, benzocarbocycle or heterocycloalkyl selected from the group consisting of (1) 2-indolyl,
(2) 3-indolyl,
(3) 1-methyl-5-indolyl
(4) 2-benzofuranyl,
(5) 3-benzofuranyl,
(6) 5-benzofuranyl,
(7) 6-benzofuranyl,
(8) 2-benzothienyl,
(9) 3-benzothienyl,
(10) 5-benzothienyl,
(11) 6-benzothienyl,

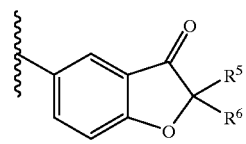 (12)

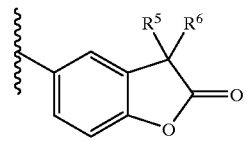 (13)

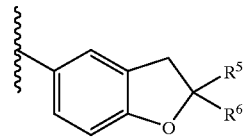 (14)

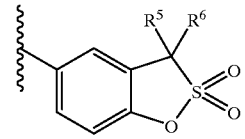 (15)

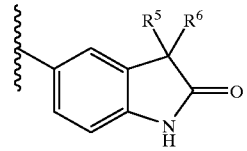 (16)

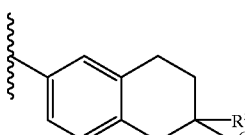 (17)

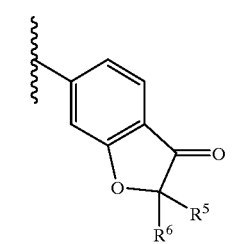 (18)

-continued
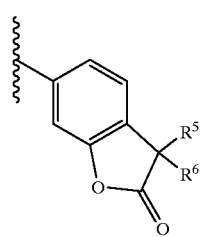 (19)
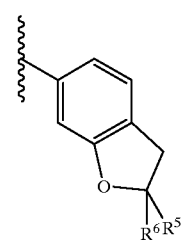 (20)
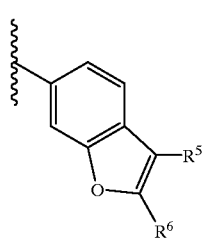 (21)
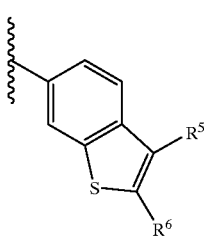 (22)
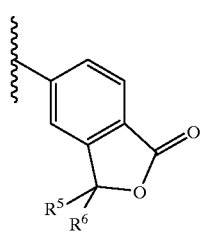 (23)
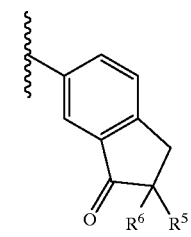 (24)
-continued
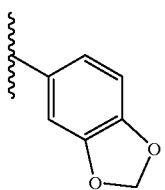 (25)
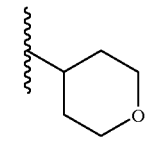 (26)
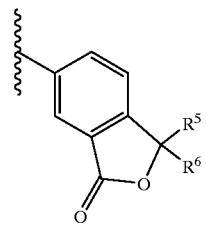 (27)
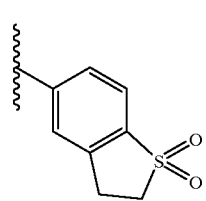 (28)
 (29)
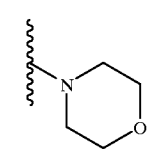 (30)
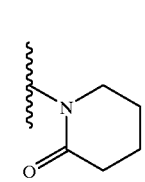 (31)
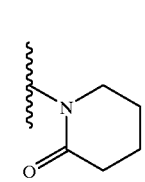 (32)

(33)

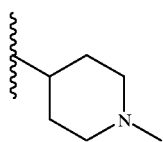

wherein said substituents are selected from the group consisting of
(1) hydrogen,
(2) halo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —C($R^5$)($R^6$)—OH, and
(10) —C($R^5$)($R^6$)—O—$C_{1-4}$alkyl.

9. A compound according to claim 8 wherein
$R^2$ is a mono or di substituted heteroaryl wherein heteroaryl is selected from the group consisting of
(1) furanyl,
(2) diazinyl, triazinyl, tetrazinyl,
(3) imidazolyl,
(4) isooxazolyl,
(5) isothiazolyl,
(6) oxadiazolyl,
(7) oxazolyl,
(8) pyrazolyl,
(9) pyrrolyl,
(10) thiadiazolyl,
(11) thiazolyl,
(12) thienyl,
(13) triazolyl, and
(14) tetrazolyl,
wherein the substitutents are selected from the group consisting of
(1) hydrogen,
(2) fluoro or chloro,
(3) $C_{1-3}$alkoxy,
(4) $C_{1-6}$alkylthio,
(5) CN,
(6) $CF_3$,
(7) $C_{1-3}$alkyl,
(8) —C($R^5$)($R^6$)—OH;
(9) —C($R^5$)($R^6$)—O—$C_{1-4}$alkyl.

10. A compound according to claim 9 wherein
$R^2$ is a mono or di substituted heteroaryl wherein heteroaryl is selected from the group consisting of
(1) 2-furanyl,
(2) 3-furanyl,
(3) 2-thienyl,
(4) 3-thienyl,
(5) 3-isoxazolyl,
(6) 4-isoxazolyl,
(7) 5-isoxazolyl,
(8) 3-isothiazolyl,
(9) 4-isothiazolyl,
(10) 5-isothiazolyl,
(11) 2-oxazolyl,
(12) 4-oxazolyl,
(13) 5-oxazolyl,
(14) 2-thiazolyl,
(15) 4-thiazolyl,
(16) 5-thiazolyl,
(17) 1,2,3-thiadiazol-4-yl,
(18) 1,2,3-thiadiazol-5-yl,
(19) 1,2,4-thiadiazol-3-yl,
(20) 1,2,4-thiadiazol-5-yl,
(21) 1,3,4-thiadiazol-2-yl,
(22) 1,2,5-thiadiazol-3-yl,
(23) 1,2,3-oxadiazol-4-yl,
(24) 1,2,3-oxadiazol-5-yl,
(25) 1,2,4-oxadiazol-3-yl,
(26) 1,2,4-oxadiazol-5-yl,
(27) 1,3,4oxadiazol-2-yl,
(28) 1,2,5-oxadiazol-3-yl,
(29) pyrazol-4-yl,
(30) pyrazol-5-yl,
(31) 1,2,3-triadiazol-4yl,
(32) 1,2,3-triadiazol-5-yl,
(33) 1,2,4-triadiazol-3-yl,
(34) 1,2,4triadiazol-5-yl,
(35) 1,2-diazinyl,
(36) 1,3-diazinyl,
(37) 1,4-diazinyl,
(38) 1,2,3,4-tetrazin-5-yl,
(39) 1,2,4,5-tetrazin-4-yl,
(40) 1,3,4,5-tetrazin-2-yl, and
(41) 1,2,3,5-tetrazin-4-yl.

11. A compound according to claim 10 wherein
$R^2$ is a mono or di substituted heteroaryl wherein heteroaryl is selected from the group consisting of
(1) 3-isoxazolyl,
(2) 4-isoxazolyl,
(3) 5-isoxazolyl,
(4) 3-isothiazolyl,
(5) 4-isothiazolyl,
(6) 5-isothiazolyl,
(7) 2-oxazolyl,
(8) 4-oxazolyl,
(9) 5-oxazolyl,
(10) 2-thiazolyl,
(11) 4-thiazolyl,
(12) 5-thiazolyl,
(13) 1,2,3-thiadiazol-4-yl,
(14) 1,2,3-thiadiazol-5-yl,
(15) 1,2,4-thiadiazol-3-yl,
(16) 1,2,4-thiadiazol-5-yl,
(17) 1,3,4-thiadiazol-2-yl,
(18) 1,2,5-thiadiazol-3-yl,
(19) 1,2,3-oxadiazol-4-yl,
(20) 1,2,3-oxadiazol-5-yl,
(21) 1,2,4oxadiazol-3-yl,
(22) 1,2,4-oxadiazol-5-yl,
(23) 1,3,4oxadiazol-2-yl,
(24) 1,2,5-oxadiazol-3-yl,
(25) 1,2-diazinyl,
(26) 1,3-diazinyl, and
(27) 1,4-diazinyl.

12. A compound according to claim 11 wherein
the hetreoaryl is selected from the group consisting of
(1) 3-isothiazolyl,
(2) 4-isothiazolyl,
(3) 5-isothiazolyl,
(4) 2-oxazolyl,
(5) 4-oxazolyl,
(6) 5-oxazolyl,
(7) 2-thiazolyl,
(8) 4-thiazolyl,
(9) 5-thiazolyl,

(10) 1,2-diazinyl,
(11) 1,3-diazinyl, and
(12) 1,4-diazinyl, and
wherein the substitutents are selected from the group consisting of
(1) hydrogen,
(2) fluoro or chloro,
(3) $C_{1-3}$alkoxy,
(4) $C_{1-3}$alkylthio,
(5) CN,
(6) $C_{1-3}$alkyl, and
(7) —C($R^5$)($R^6$)—OH,
$R^3$ is $CH_2OR^7$, CN, $CH_2CN$, or $C_{1-3}$fluoroalkyl;
$R^4$ is
(a) substituted phenyl or substituted heteroaryl, said substituents are selected from the group consisting of
(1) hydrogen
(2) halo, including fluoro, chloro, bromo and iodo,
(3) $C_{1-3}$alkyl,
(4) $C_{1-3}$alkoxy,
(5) $C_{1-4}$alkylthio,
(6) CN,
(7) $CF_3$, or
(b) $C_{1-3}$alkyl, $CH_2OR^7$, CN, $CH_2CN$, or $C_{1-3}$fluoroalkyl;
$R^5$ and $R^6$ are each independently hydrogen, methyl or ethyl.

13. A compound selected from the group consisting of:

(a) 3-(Benzo[1,3]dioxol-5-yl)-5,5-dimethyl-4-(4-(methylsulfonyl)phenyl)-2-(5H)-furanone,
(b) 5,5-Dimethyl-3-cyclohexyl-4-(4-(methylsulfonyl)phenyl)-2-(5H)-furanone,
(c) 4-(4-(Methylsulfonyl)phenyl)-3-phenyl-1-oxa-spiro[4,4]non-3-en-2-one,
(d) 7-(4-(methylsulfonyl)phenyl)-6-phenyl-4-oxa-spiro[2,4]-hept-6-en-5-one, and
(e) 5,5-Bis(fluoromethyl)-3-phenyl-4-(4-(methylsulfonyl)phenyl)-2-(5H)-furanone.

14. A pharmaceutical composition comprising:
a compound according to claim 1 and a pharmaceutically acceptable carrier.

15. A pharmaceutical composition for treating cyclooxygenase mediated diseases treated by an active agent that selectively inhibits COX-2 in preference to COX-1 comprising:
a non-toxic therapeutically effective amount of a compound according to claim 1 and a pharmaceutically acceptable carrier.

16. A method of treating an inflammatory disease susceptable to treatment with an non-steroidal anti-inflammatory agent comprising:
administration to a patient in need of such treatment of a non-toxic therapeutically effective amount of a compound according to claim 1 and a pharmaceutically acceptable carrier.

17. A method of treating cyclooxygenase mediated diseases treated by an active agent that selectively inhibits COX-2 in preference to COX-1comprising:
administration to a patient in need of such treatment of a non-toxic therapeutically effective amount of a compound according claim 1.

18. A method of treating inflammation in a patient for which non-steroidal antiiflammatory drugs may be contraindicated comprising:
administration to a patient in need of such treatment of a non-toxic therapeutically effective amount of a compound according to claim 1 and a pharmaceutically acceptable carrier.

19. A compound selected from the group consisting of:

(a) 3-(3,5-Difluoro-phenyl)-4-(4-methylsufonyl-phenyl)-1-oxa-spiro[4.4]non-3-en-2-one,
(b) 3-Chroman-7-yl-5,5-dimethyl-4-(4-methylsulfonyl-phenyl)-5H-furan-2-one,
(c) 8-(4-Methylsulfonyl-phenyl)-7-phenyl-5-oxa-spiro[3.4]oct-7-en-6-one,
(d) 6-(3-Fluorophenyl)-7-(4-(methylsulfonyl)phenyl)-4-oxa-spiro[2.4]hept-6-en-5-one,
(e) 7-(4-Methylsulfonylphenyl)-6-naphthalen-2-yl-4-oxa-spiro[2.4]hept-6-en-5-one,
(f) 4-(6-Naphthalen-2-yl-5-oxo-4-oxa-spiro[2.4]hept-6-en-7-yl)-benzenesulfonamide,
(g) 7-(4-Fluorophenyl)-8-(4-methylsulfonylphenyl)-5-oxa-spiro[3.4]oct-7-en-6-one,
(h) 7-(3-Fluorophenyl)-8-(4-methylsulfonylphenyl)-5-oxa-spiro[3.4]oct-7-en-6-one,
(i) 7-(3,4-Difluorophenyl)-8-(4-methylsulfonylphenyl)-5-oxa-spiro[3.4]oct-7-en-6-one,
(j) 4-(6-Oxo-7-phenyl-5-oxa-spiro[3.4]oct-7-en-8-yl)-benzenesulfonamide,
(k) 4-[7-(4-Fluorophenyl)-6-oxo-5-oxa-spiro[3.4]oct-7-en-8-yl]-benzenesulfonamide,
(l) 4-[7-(3-Fluorophenyl)-6-oxo-5-oxa-spiro[3.4]oct-7-en-8-yl]-benzenesulfonamide,
(m) 4-[7-(3,4-Difluorophenyl)-6-oxo-5-oxa-spiro[3.4]oct-7-en-8-yl]-benzenesulfonamide,
(n) 3-(4-Fluorophenyl)-4-(4-(methylsulfonyl)phenyl)-1-oxa-spiro[4.4]non-3-en-2-one,
(o) 3-(3-Fluorophenyl)-4-(4-(methylsulfonyl)phenyl)-1-oxa-spiro[4.4]non-3-en-2-one,
(p) 3-(3,4-Difluorophenyl)-4-(4-(methylsulfonyl)phenyl)-1-oxa-spiro[4.4]non-3-en-2-one,
(q) 3-(3-Chloro-4-fluorophenyl)-4-(4-(methylsulfonyl)phenyl)-1-oxa-spiro[4.4]non-3-en-2-one,
(r) 4-(2-Oxo-3-phenyl-1-oxa-spiro[4.4]non-3-en-4-yl)-benzenesulfonamide,
(s) 4-[3-(4-Fluorophenyl)-2-oxo-1-oxa-spiro[4.4]non-3-en-4-yl)]-benzenesulfonamide,
(t) 4-[3-(3-Fluorophenyl)-2-oxo-1-oxa-spiro[4.4]non-3-en-4-yl)]-benzenesulfonamide,
(u) 4-[3-(3,4-Difluorophenyl)-2-oxo-1-oxa-spiro[4.4]non-3-en-4-yl)]-benzenesulfonamide,
(v) 4-[3-(3-Chloro-4-fluorophenyl)-2-oxo-1-oxa-spiro[4.4non-3en-4yl]-benzenesulfonamide,
(w) 4-(4-(Methylsulfonyl)phenyl)-1-oxa-spiro[4.5]dec-3-en-2-one,
(x) 4-(2-Oxo-3-phenyl-1-oxa-spiro[4.5]dec-3-en-4-yl)-benzenesulfonamide, and
(y) 4-[3-(4-Fluorophenyl)-2-oxo-1-oxa-spiro[4.5]dec-3-en-4-yl)-benzenesulfonamide.

20. A compound which is 3-(3-Allyloxy-phenyl)-5,5-dimethyl-4-(4-methylsulfonyl-phenyl)-5H-furan-2-one.

* * * * *